United States Patent
Vicente et al.

(10) Patent No.: US 7,067,653 B2
(45) Date of Patent: Jun. 27, 2006

(54) PORPHYRIN BASED NEUTON CAPTURE AGENTS FOR CANCER THERAPY

(75) Inventors: Maria Da Graca H. Vicente, Baton Rouge, LA (US); Shankar Jayaram Shetty, Maharastra (IN); Laurent Jaquinod, Davis, CA (US); Kevin M. Smith, Baton Rouge, LA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/258,948

(22) PCT Filed: May 9, 2001

(86) PCT No.: PCT/US01/15433

§ 371 (c)(1),
(2), (4) Date: Apr. 2, 2003

(87) PCT Pub. No.: WO01/85736

PCT Pub. Date: Nov. 15, 2001

(65) Prior Publication Data

US 2004/0014737 A1    Jan. 22, 2004

Related U.S. Application Data

(60) Provisional application No. 60/203,160, filed on May 9, 2000.

(51) Int. Cl.
*C07D 487/22* (2006.01)
*C07F 5/02* (2006.01)

(52) U.S. Cl. .................. 540/145; 514/64; 568/1; 568/3; 568/4; 568/5; 568/6

(58) Field of Classification Search ............ 568/3, 568/5, 6, 1, 4; 514/64; 540/145
See application file for complete search history.

(56) References Cited

U.S. PATENT DOCUMENTS 4,959,356 A * 9/1990 Miura et al. .............. 424/1.81
5,877,165 A * 3/1999 Miura et al. .................. 514/64

OTHER PUBLICATIONS

Draetta, G. and Pagano, M. in "Annual Reports in Medicinal Chemistry, vol. 31", 1996, Academic Press, San Diego, p. 241-248.*
Wyzlic, Iwona M.; Tjarks, Werner; Soloway, Albert H.; Perkins, Douglas J.; Burgos, Minerva; O'Reilly, Kevin P., Inorganic Chemistry, 35(16), 4541-4547 (English) 1996.*
Nemoto, Hisao; Rong, Feng Guang; Yamamoto, Yoshinori, Journal of Organic Chemistry, 55(25), 6065-6 (English) 1990.*
Aldrich Chemical Company, Inc., Milwaukee, WI, 1992, p. 1043.*

Callahan, D.E. et al. "Boronated Protoporphyrin (BOPP): Localization in Lysosomes of the Human Glioma Cell Line SF-767 with Uptake Modulated by Lipoprotein Levels." *Int. J. Radiation Oncology Biol. Phys.* 45(3):761-771 (1999).
Ceberg. C. et al. "A comparative study on the pharmacokinetics and biodistribution of boronated porphyrin (BOPP) and sulfhydryl boron hydride (BSH) in the RG2 rat glioma model." *J. Neurosurg* 83:86-92 (1995).
Fairchild, R.G. et al. "*In Vitro* Determination of Uptake, Retention, Distribution, Biological Efficacy, and Toxicity of Boronated Compounds for Neutron Capture Therapy: A Comparison of Porphyrins with Sulfhydryl Boron Hydrides." *Cancer Research* 50:4860-4865 (1990).
Hill, J.S. et al. "Selective tumor kill of cerebral glioma by photodynamic therapy using a boronated porphyrin photosensitizer." *Proc. Natl. Acad. Sci. USA* 92:12126-12130 (1995).
Matsumura, A. et al. "A new boronated porphyrin (STA-BX909) for neutron capture therapy: an in vitro survival assay and in vitro tissue uptake study." *Cancer Letters* 141:203-209 (1999).
Miura, M. et al. "Preparation Of Carboranyl Porphyrins for Boron Neutron Capture Therapy." *Tetrahedron Letters* 31(16):2247-2250 (1990).

(Continued)

Primary Examiner—Thomas C. McKenzie
(74) Attorney, Agent, or Firm—Fulbright & Jaworski

(57) ABSTRACT

The invention describes the synthesis of a panel of novel carbon-carbon linked carboranyl-containing 5,10,15,20-tetraphenylporphyrins bearing 25–44% boron by weight. In certain embodiments, a phenyl porphyrin compound has a carboranyl group attached to the phenyl group by a carbon-carbon linkage, wherein the phenyl group corresponds to the following formula

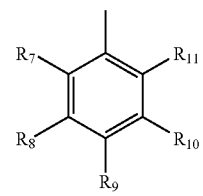

where R7 through R11 are hydrogen, a carboranyl group, or are selected from the group consisting of hydroxyl, $NMe_3^+$, $PMePh_2^+$, $PO(OH)_2$, $SO_3H$, $COOH$, and $NH_2$. In this embodiment, the carboranyl group is attached to the phenyl group by a carbon-carbon linkage, either one or two of R7 through R11 are other than hydrogen; and the phenyl porphyrin compound contains at least one phenyl group having at least one of said carboranyl groups.

23 Claims, 8 Drawing Sheets

OTHER PUBLICATIONS

Miura, M. et al. "Evaluation of carborane-containing porphyrins as tumour targeting agents for boron neutron capture therapy." *The British Journal of Radiology* 71:773-781 (1998).

Munday, A.D. et al. "Mitochondria are the functional intracellular target for a photosensitizing boronated porphyrin." *Biochimica et Biophysica Acta* 1311:1-4 (1996).

Phadke, A.S. et al. "Synthesis of Carboranyl Porphyrins: Potential Drug for Boron Neutron Capture Therapy." *Tetrahedron Letters* 34(11):1725-1728 (1993).

Tibbitts, J. et al. "Plasma Pharmacokinetics and Tissue Biodistribution of Boron Following Administration of a Boronated Porphyrin in Dogs." *Journal of Pharmaceutical Sciences* 89(4):469-477 (2000).

Tibbitts, J. et al. "Toxicology of a Boronated Porphyrin in Dogs." *Photochemistry and Photobiology* 69(5):587-594 (1999).

Vicente, M.G.H. "Porphyrin-based Sensitizers in the detection and Treatment of Cancer: Recent Progress." *Curr. Med. Chem.—Anti-Cancer Agents* 1(2):175-194 (2001).

Woodburn, K. et al. "An *In Vitro* Study of Boronated Porphyrins for Potential Use in Boron Neutron Capture Therapy." *Bioorganic and Medicinal Chemistry Letters* 3(10):2017-2022 (1993).

Zakharkin, L.I. et al. "Synthesius of carboranyl drivatives of deuteroporphyrin IX." *Russian Chemical Bulletin* 48(12):2312-2314 (1999).

* cited by examiner

PORPHYRIN BASED NEUTON CAPTURE AGENTS FOR CANCER THERAPY

This application claims the benefit of Provisional Application No. 60/203,160, filed May 9, 2000.

STATEMENT REGARDING FEDERALLY SPONSORED RESEARCH AND DEVELOPMENT

This invention was made with Government support under Grant No. 98ER62633, awarded by the Department of Energy. The Government has certain rights to this invention.

FIELD OF THE INVENTION

The field of the invention is cancer therapy.

BACKGROUND OF THE INVENTION

Boron neutron capture therapy (BNCT) is a bimodal modality for cancer treatment consisting on the irradiation of $^{10}$B-rich tumors with low-energy (thermal) neutrons, with subsequent production of high linear energy transfer particles, $^{4}$He$^{2+}$ (alpha-particle) and $^{7}$Li$^{3+}$, which cause severe damage to tumor cells through ionization processes; see Barth, Soloway, Fairchild et al., infra; Barth, Soloway, Goodman et al., infra. Because the cytotoxic ions produced in the nuclear reaction have a limited distance of travel in tissue (approximately one cell diameter, 5–9 μm), the success of this modality for cancer therapy depends on the selective uptake of boron in the tumor cells; see Hawthorne, (1998), infra; Hawthorne, (1993). infra. Malignant brain tumors are responsible for more than 10,000 deaths per year in the United States, and BNCT is specially attractive as the treatment because it potentially targets and destroys malignant cells in the presence of normal cells, thus, preventing undesirable side effects common in other types of treatments. In addition, BNCT has advantages over photoradiation therapy in that neutron beams can penetrate upwards of ten times deeper, to reach deep-seated tumor sites (6–7 cm).

In recent years, several research groups have developed a variety of new $^{10}$B carriers with improved tumor selectivity over the two boron neutron capture agents currently undergoing clinical trials in the U.S., Europe, and Japan, for the treatment of patients with glioblastomas and melanomas disodium mercapto-closo-dodecaborate (BSH) and L-4-dihydroxy-borylphenylalanine (BPA). See Kageji, et al., infra. Pignol, et al., infra; Elowitz, et al., infra. To date, of all the new boron-delivery agents, porphyrins are particularly promising tumor-selective compounds because of their natural tendency to accumulate in neoplastic tissue; see Bonnett, infra. This property of porphyrins provides the basis for their use in another therapeutic method, the photodynamic therapy (PDT) of tumors; see Schnitmaker, et al., infra; Dougherty, et al., infra. PDT relies on the selective uptake of a photosensitizer in tumor tissues, followed by generation of singlet oxygen and other cytotoxic species upon irradiation with red light. Photofrin®, a porphyrin derivative and only FDA-approved PDT drug has been used to treat thousands of patients in Canada, Europe, Japan and U.S. with early and advanced stage cancer of the lung, digestive tract, and genitourinary tract. In addition to necrosis as the result of oxidative damage, it has been recently shown that some porphyrins also induce apoptosis (programmed cell death), either upon irradiation with light (particularly at low light doses), or by accumulation of high drug levels in tissues, in the dark.; see Luo, Chang, et al., infra; Luo, Ke, et al., infra. The ability of porphyrin-PDT to induce apoptosis may also be an important element for the success of both PDT and BNCT modalities for cancer treatment. Photofrin® presents the disadvantages of being a complex mixture of compounds of variable composition. Thus, active research in the area of development of new and highly efficient PDT photosensitizers is underway. Also, boron-containing porphyrin derivatives that selectively localize in tumor cells have potential PDT applications; see Hill, Kahl, Stylli et al., infra.

Porphyrins and their diamagnetic metal complexes are highly fluorescent. This provides a means for detection of tumor cells and for investigation of the $^{10}$B localization in tumors and surrounding tissues; see Mang et al., infra.

Intracellular boron distribution and quantification play important roles in determining the dose and length of a neutron radiation period, as well as the success of BNCT treatment; see Nigg et al., infra. The intracellular localization of porphyrins is highly dependent upon their physicochemical properties, including structural features such as nature of peripheral side chains, hydrophobicity, charge, molecular weight, and amphiphilic character; see Woodburn, Vardaxis, et al., infra. Certain porphyrins have been reported to have the ability to target the nuclei of tumor cells and causing DNA damage through intercalation, or binding to DNA; see Munson and Fiel, infra; Schneider and Wang, infra; Ding et al., (1991), infra; Sari et al., infra; Penning et al., infra. Therefore, the newly developed BNCT agents will display an appropriate balance between hydrophobicity and hydrophilicity. This property will give adequate solubility in aqueous or biological media, and enhanced interaction with cell membranes.

Although BSH and BPA have been shown to be safe and efficacious in animal models, BSH is reported to be sensitive to air-oxidation (Tolpin et al., infra) and both BSH and BPA have only moderate selectivity for tumor cells and low retention times in tissues (Capala et al., infra). The ultimate success of BNCT is dependent upon whether adequate concentrations of boron-containing capture agents and low-energy neutrons can be selectively and effectively delivered to tumor cells. Since selective production of epithermal neutrons with high beam quality has been achieved by modern nuclear reactors (such as the one available at the McClellan Nuclear Radiation Center in Sacramento), the main unsolved problem in BNCT centers on the development of new effective $^{10}$B carriers, capable of selectively delivering substantial concentrations of $^{10}$B atoms to tumors. In the last ten years, several boron-containing porphyrin derivatives have been reported for application in BNCT and their in vitro and in vivo properties evaluated; see Hill, Kahl, Kaye et al., infra; Woodburn, Phadke et al., infra; Ceberg et al., infra; Ozawa et al., infra; Miura, Micca, et al., infra; Matsumura et al., infra. These studies reveal that boronated porphyrins accumulate within cells of glioma models to a much greater extent, and are retained for longer periods of time, than do BSH and BPA. In addition, along with low toxicities and favorable intracellular biodistributions, significantly higher tumor porphyrin ratios relative to blood and normal tissue are found for some of these boronated porphyrins. To date, amongst the porphyrin-based BNCT drugs reported, in vivo investigations with BOPP (a protoporphyrin-IX derivative) and NiTCP-H (a meso-tetraphenylporphyrin derivative) are the most promising; see Kahl and Koo, infra; Miura, Gabel et al., infra. BOPP contains four carboranyl residues linked by ester bonds to the porphyrin macrocycle. In vivo cleavage of such linkages has been accounted for the sometimes observed low retention times of this drug in tumor cells. The highly lipophilic NiTCP-H contains four ether-linked carboranyl moieties, and requires the use of solubilizing agents such as Cremophor EL (a polyethoxylated castor oil) and propylene glycol as delivery vehicles; secondary effects of these solubilizing agents are not yet well understood; see Woodcock et al., infra; Badary et al., infra. Other boron-containing porphyrins are reported in the literature, but they contain a lower percentage (5–15%) of boron by weight.

SUMMARY OF THE INVENTION

The present invention describes novel benzaldehyde intermediates for use the synthesis of novel carboranyl-containing 5,10,15,20-tetraphenylporphyrins. The new compounds feature carbon-carbon linkages between the carboranyl groups and the phenyl groups of the mesophenylporphyrin ring; and up to about 25–44% boron by weight. The present invention also includes methods and compositions for using the carboranyl-containing porphyrins in cancer treatments involving boron neutron capture therapy or photodynamic therapy.

DETAILED DESCRIPTION

Figure 1:
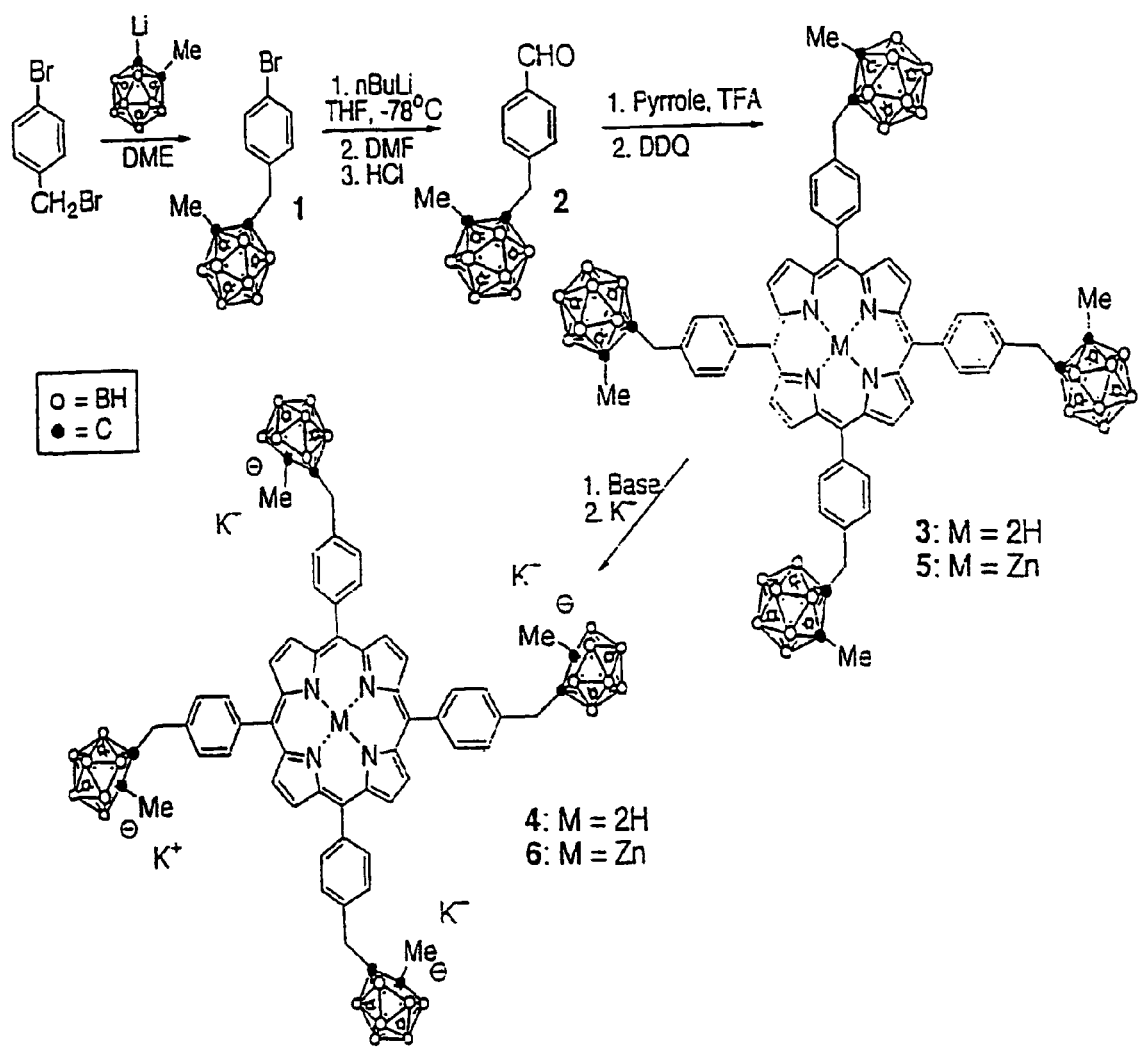
FIG. 1 describes the synthesis of compounds 1–6.
Figure 2:
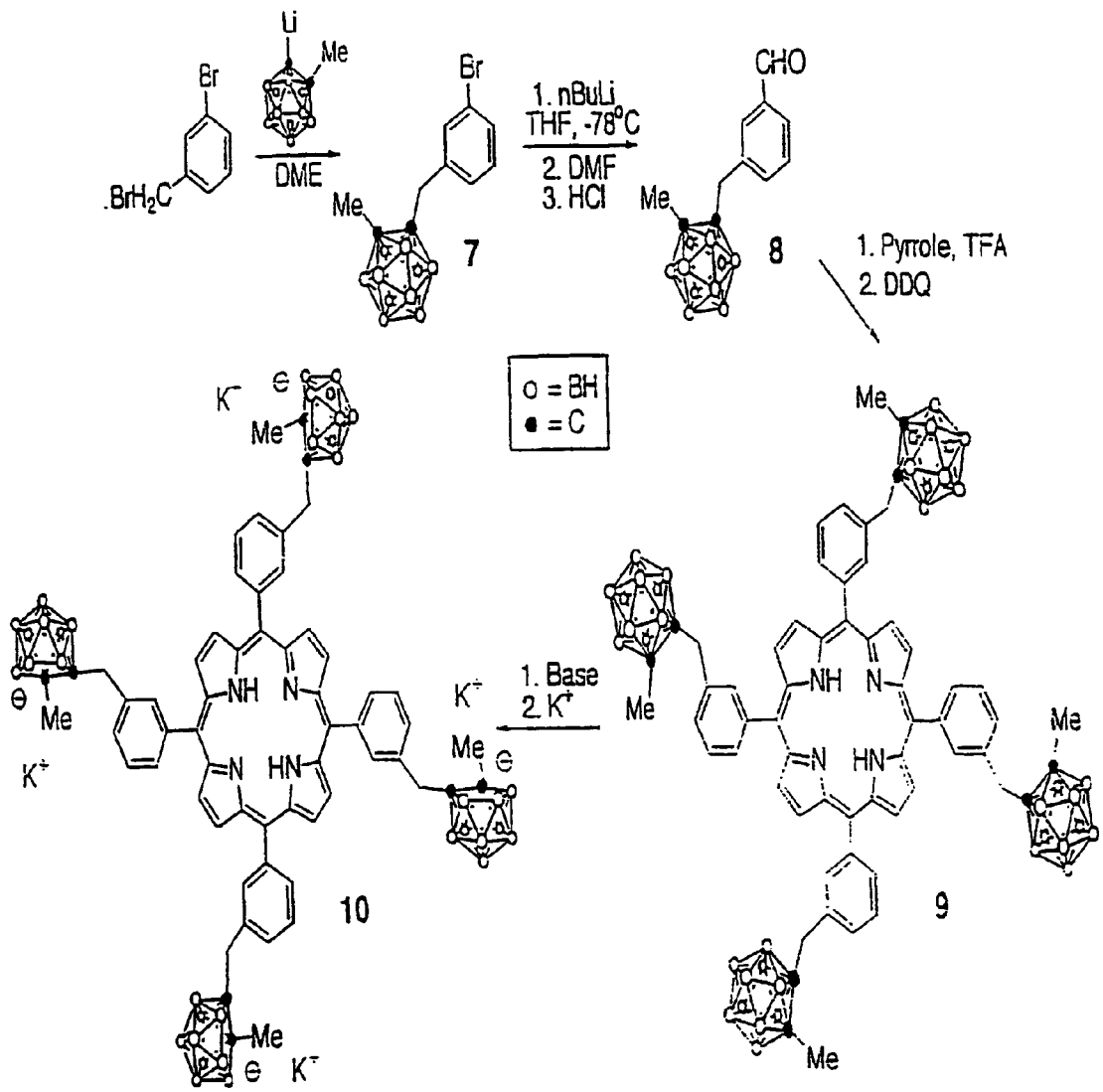
FIG. 2 describes the synthesis of compounds 7–10.
Figure 3:
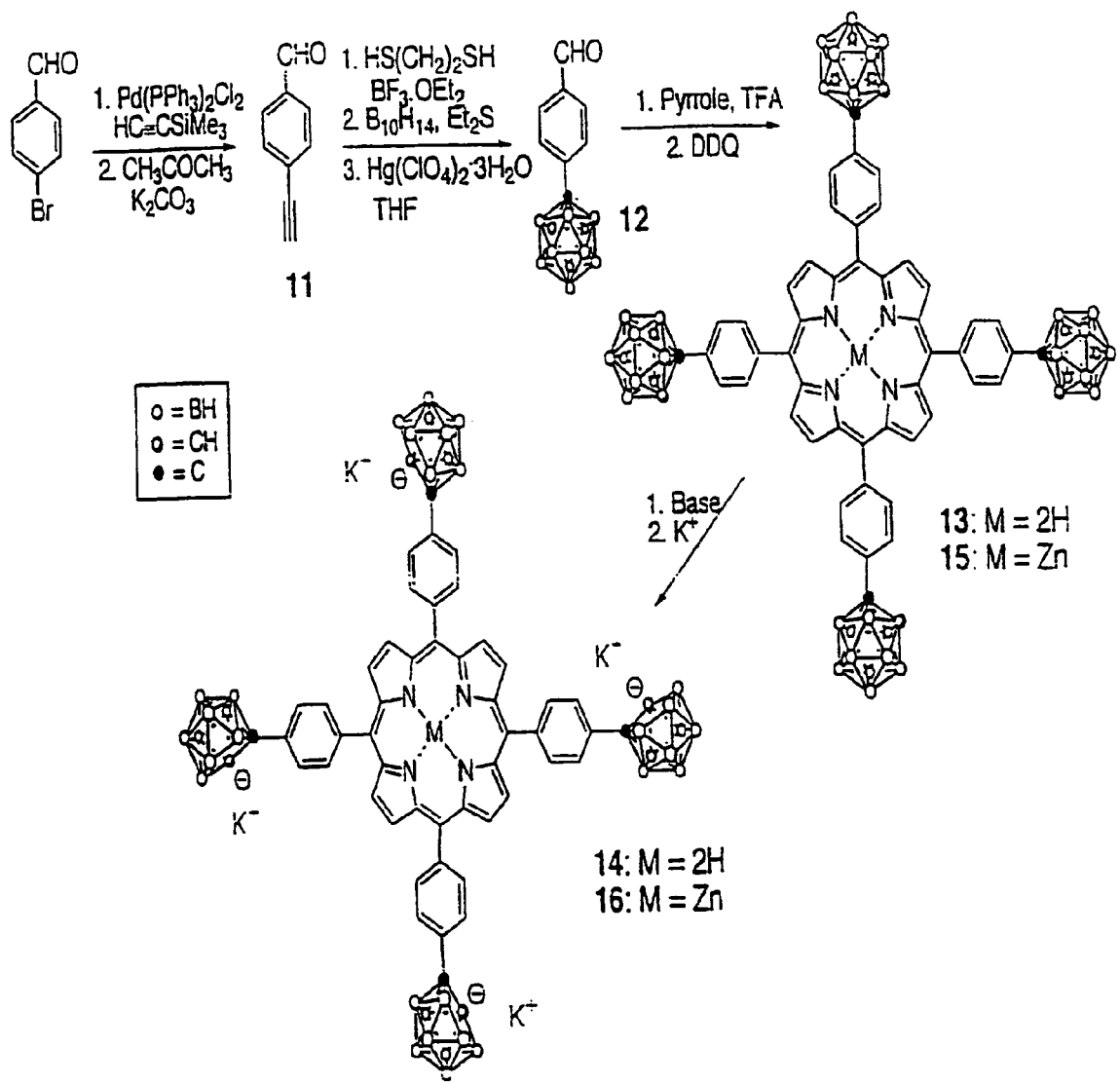
FIG. 3 describes the synthesis of compounds 11–16.
Figure 4:
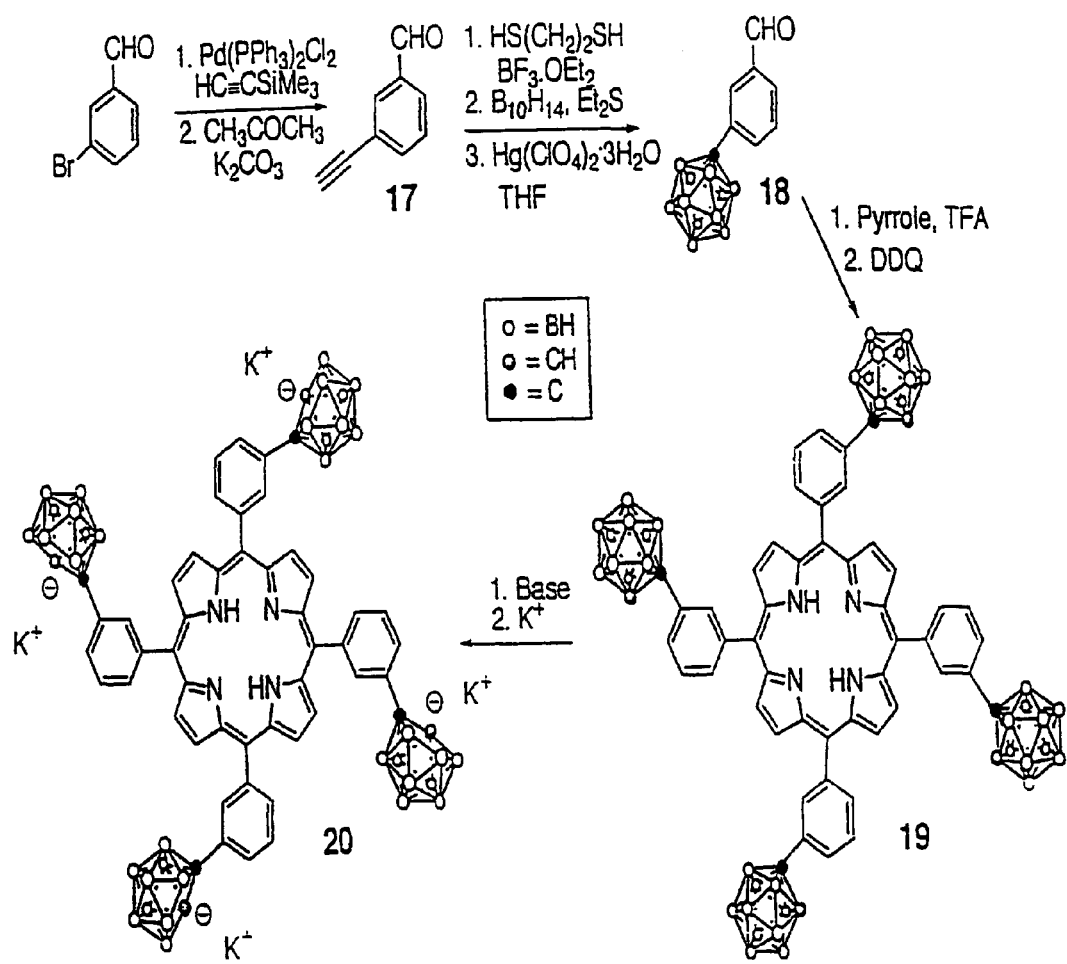
FIG. 4 describes the synthesis of compounds 17–20.
Figure 5:
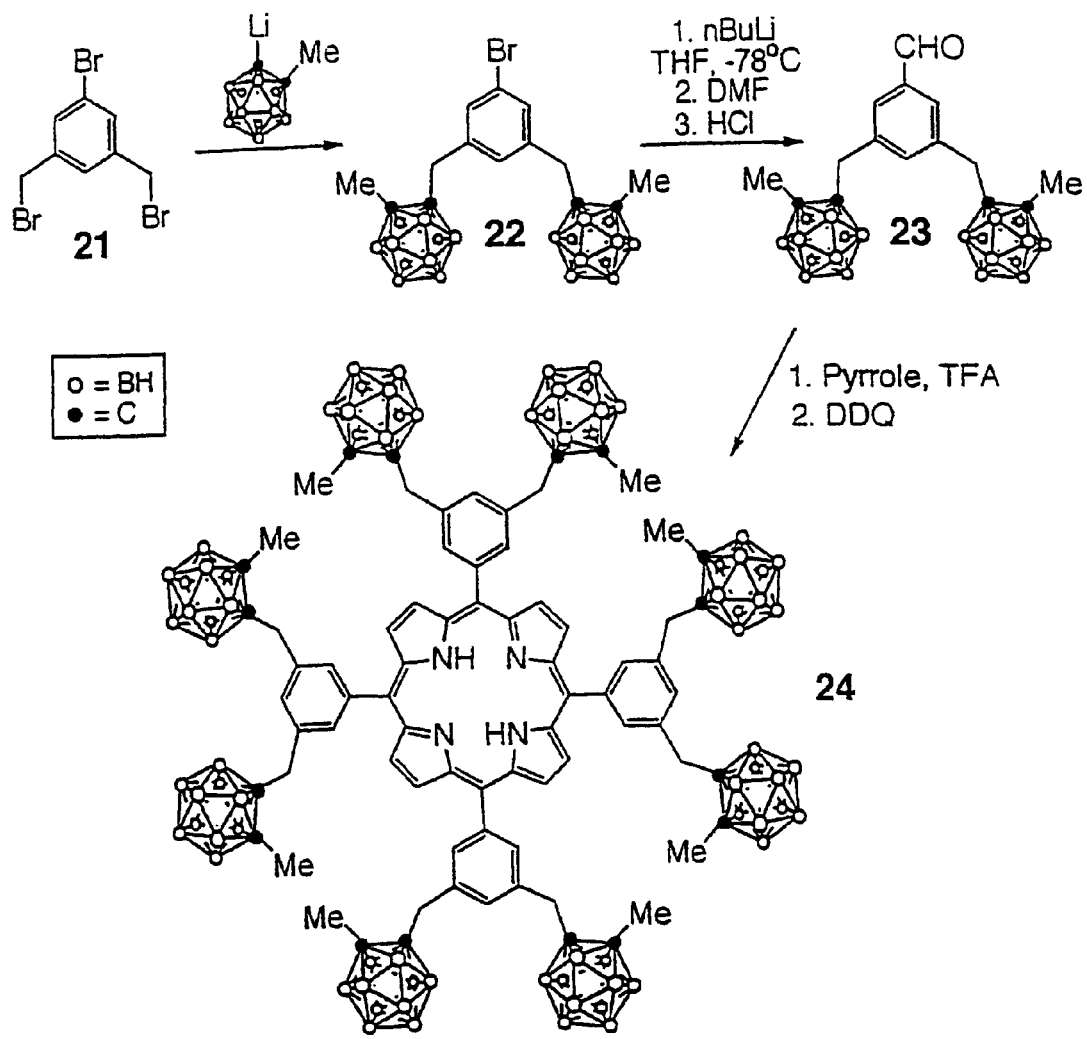
FIG. 5 describes the synthesis of compounds 21–24.

The present invention is directed to the synthesis and use of porphyrin compounds, which contain carboranyl groups attached to the porphyrin compound by a carbon-carbon linkage. The porphyrin compound generally corresponds to general formula I:

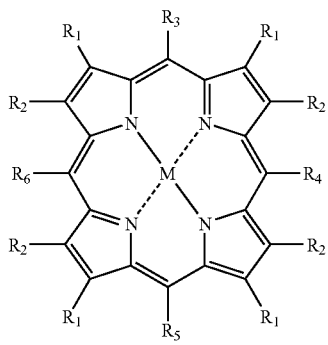

where M is 2H or a divalent metal ion; R1 and R2 are each independently hydrogen, alkyl or hydoxyalkyl; and R3 through R6 are hydrogen or a substituted phenyl group.

The substituted phenyl group corresponds to general formula II:

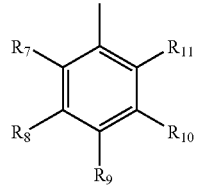

where R7 through R11 are hydrogen, a hydrophilic group or a carboranyl group. The carboranyl group is attached to the phenyl group by a carbon-carbon linkage. Typically, either one or two of R7 through R11 are hydrophilic or carboranyl groups. Examples of hydrophilic groups include hydroxyl, $NMe_3^+$, $PMePh_2^+$, $PO(OH)_2$, $SO_3H$, $COOH$ or $NH_2$.

At least one of R3 through R6 is a phenyl group of general formula II having at least one carboranyl group attached by a carbon-carbon linkage. More preferably, two of R3 through R6 are phenyl groups of general formula II, each having at least one carboranyl group. Most preferably, R3 through R6 are all phenyl groups of general formula II, each having at least one carboranyl group.

In a preferred embodiment of the porphyrin compound the carboranyl group is 1-methyl-o-carboranyl or o-carboranyl. In another preferred embodiment the compound is at least about 15% boron by weight; most preferably about 25% to about 44% boron by weight.

The present invention also includes a method of making the foregoing carboranyl-containing porphyrin compounds.

The first step of the method is providing a reaction mixture, which includes (1) a pyrrole or a dipyrrole, and (2) a benzaldehyde, both dissolved in a suitable solvent. The pyrrole or dipyrrole can be unsubstituted or substituted with alkyl groups; and the benzaldehyde is of general formula III

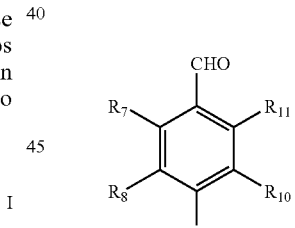

where R7 through R11 are each hydrogen, a hydrophilic group or a carboranyl group attached to the benzaldehyde by a carbon-carbon linkage. Hydrophilic groups can include hydroxyl, $NMe_3^+$, $PMePh_2^+$, $PO(OH)_2$, $P(CH_2OH)_2$, $SO_3^-$, $COOH$, $CO_2^-$ or $NH_2$.

The next step of the method is to subject the reaction mixture to an acidic pH until the benzaldehyde and the pyrrole, or the benzaldehyde and the dipyrrole, are converted to a porphyrin compound. In one preferred version of the method, the reaction mixture is subjected to an acidic pH by the addition of TFA. Preferred versions of the method also include oxidation of the reaction mixture with tetrachloroquinone or dichlorodicyanobenzoquinone.

Optionally, the method can include complexing the porphyrin compound with a divalent metal ion, e.g. by treating the free base of the porphyrin compound with zinc choride to form a Zn(II) complex. Moreover, the solubility of the porphyrin compound can be improved by forming a salt of the porphyrin compound.

The present invention also includes an intermediate for use in the synthesis of porphyrin compounds, namely the aforementioned benzaldehyde of general formula III

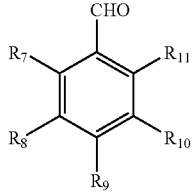

III where R7 through R11 are each hydrogen, a hydrophilic group or a carboranyl group attached to the benzaldehyde by a carbon-carbon linkage; and either one or two of R7 through R11 are carboranyl groups.

We anticipate that the carboranyl-containing porphyrins of the present invention will be of use in cancer treatments involving boron neutron capture therapy (BNCT). Accordingly, the present invention includes a method of delivering an effective amount of a neutron capture agent to tumor cells, which involves contacting the tumor cells with a carboranyl-containing porphyrin compound of the present invention. In vivo, the method includes administering the carboranyl-containing porphyrin compound to a patient, which is then selectively taken up by the tumor cells. To be effective in BNCT, the amount of porphyrin compound taken up by the tumor cells is an amount sufficient for cytotoxicity when the tumor cells are irradiated by thermal neutrons. Preferably, the tumor cells are brain tumor or melanoma cells Our preliminary results, described in greater detail in the Examples below, show that the carboranyl-containing porphyrins of the present invention will also be of use in cancer treatments involving photodynamic therapy (PDT). Thus, the present invention includes a method of delivering an effective amount of a photosensitizing agent to tumor cells, similar to the method for BNCT. In the PDT method, an effective amount of the porphyrin compound is an amount sufficient for cytotoxicity when the tumor cells are irradiated by red light.

The present invention also includes compositions for use in boron neutron capture therapy comprising an effective amount of a carboranyl-containing porphyrin compound of the present invention, and a pharmaceutically acceptable carrier or excipient. An effective amount for BNCT is an amount sufficient for selective uptake, retention and damage to tumor cells when the tumor cells are irradiated by thermal neutrons.

Similarly, the present invention includes compositions for use in photodynamic therapy comprising the carboranyl-containing porphyrin compounds of the present invention and a pharmaceutically acceptable carrier or excipient. The effective amount of the porphyrin compound for PDT is an amount sufficient for selective uptake, retention and cytotoxicity to tumor cells when the tumor cells are irradiated by red light.

FIGS. 1 through 6 describe, in very few steps, the total synthesis of carboranylated 5,10,15,20-tetraphenylporphyrins. These meso-phenylporphyrin compounds contain carbon-carbon linkages between the carboranyl groups and the meso-phenylporphyrin ring for increased chemical in vitro and in vivo stability over existing drugs. In addition, the high solubility of these new drugs in aqueous solution allows for their easy administration into the blood stream (via a concentrated saline solution of the drug), and avoids the use of a co-solvent. In vitro and in vivo biological activities of the new drugs show that these new compounds are very promising drugs for both the BNCT and the PDT modalities for cancer treatment.

Figure 6:
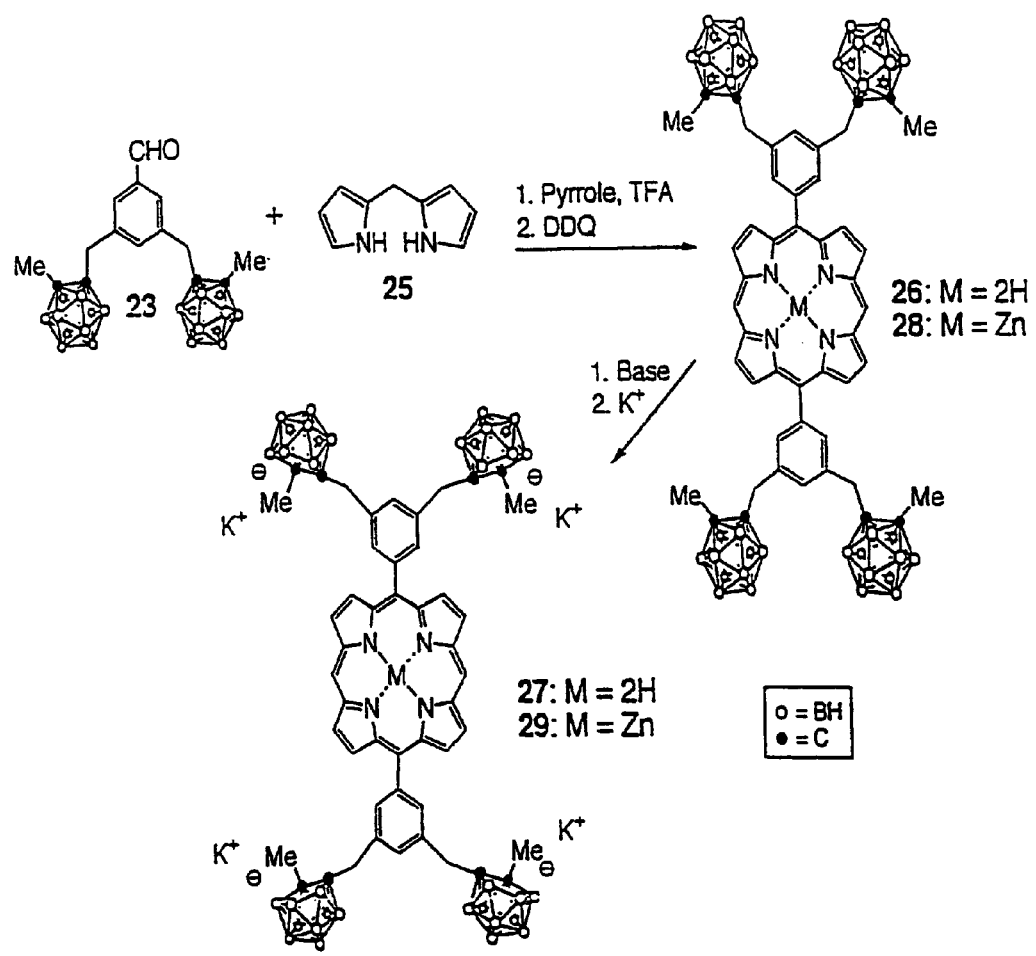
FIG. 6 describes the synthesis of compounds 25–29.
Figure 7:
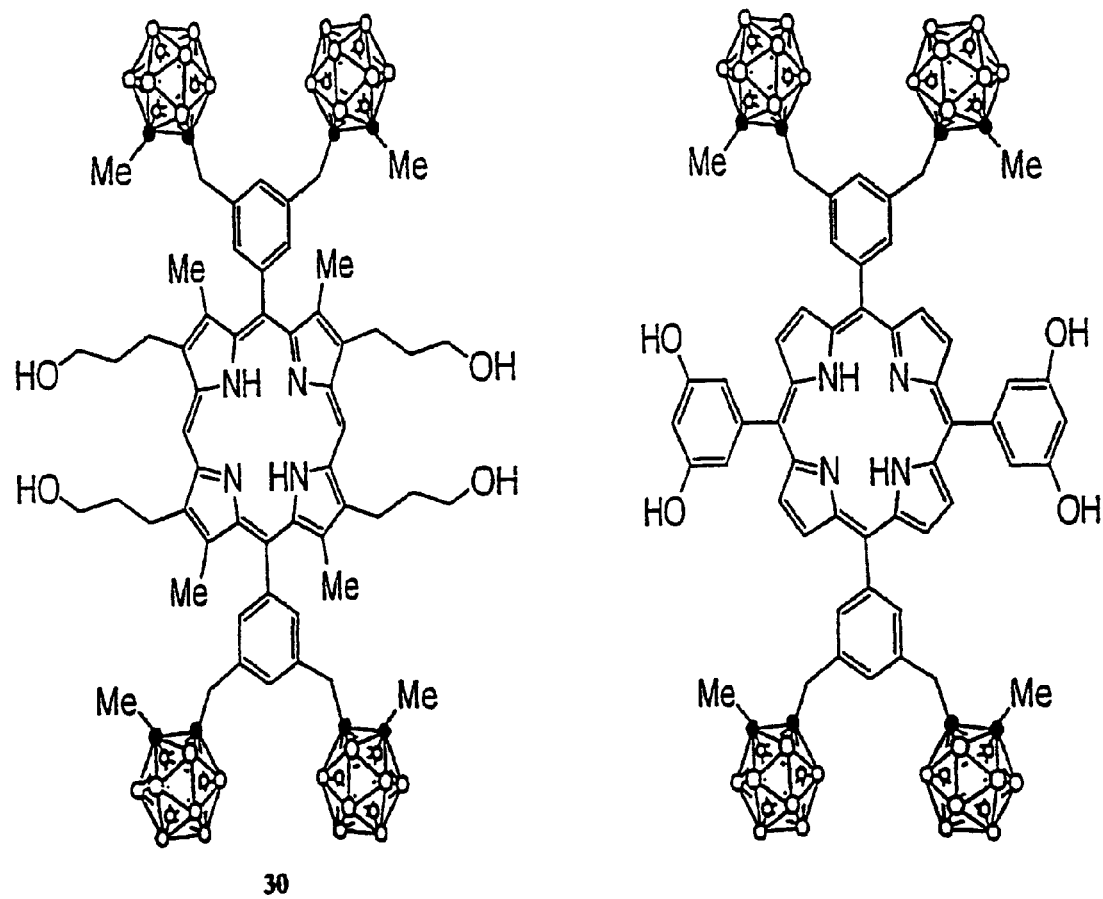
FIG. 7 describes the compounds that are synthesized using a similar methodology.
Figure 8:
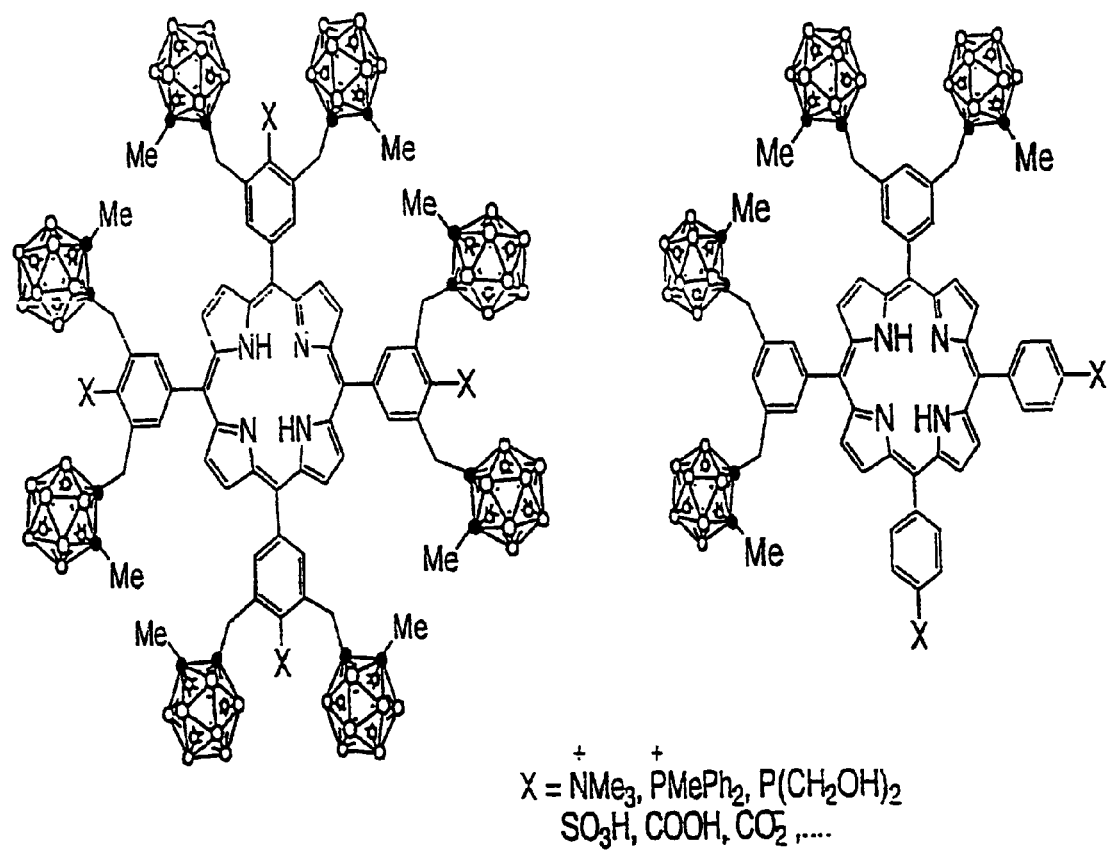
FIG. 8 describes additional compounds that can be synthesized using similar methodology.

FIG. 7 describes the compounds that can be synthesized using the same synthetic methodology as for compound 26 (FIG. 6). These unsymmetrical compounds contain carbon-carbon linked hydrophobic o-carboranyl cages and hydrophilic groups (OH) to warrant solubility in aqueous solution. FIG. 8 describes additional compounds that can be synthesized using the carborane building blocks described in FIG. 5. These compounds will be analogues of compound 24, and will bear other hydrophilic groups (neutral, positive and negative, e.g. —$NMe_3^+$, —$PMePh_2^+$, —$P(CH_2OH)_2$, $SO_3-$, $CO_2-$). In summary, all drugs in the present invention contain carbon-carbon linkages between the porphyrin ring and the carboranyl groups, and amphiphilic properties for both adequate solubility into the blood stream and interaction with cell membranes.

EXAMPLES

Synthesis of Compound 1:

[4-(1-methyl-o-carboranyl)methyl]bromobenzene (1): A two-necked round bottom flask containing 1-methyl-o-carborane (5.00 g, 31.65 mmol) in dry DME (150 mL) was cooled down to 0° C. under Argon. n-BuLi (20.0 mL, 1.6 M in hexane) was added dropwise and the resulting mixture was stirred at 0° C. for 30 minutes. A solution of 4-(bromomethyl)bromobenzene (7.91 g, 31.65 mmol) in dry DME (15 mL) was added dropwise. After stirring at 0° C. for 10 minutes, the final reaction mixture was warmed to room temperature and subsequently refluxed for 12 hours under Argon. The solvent was then removed under vacuum and the crude solid obtained was purified by recrystallization from dichloromethane/methanol to give the title compound (7.80 g, 75.4% yield) as white crystals. MS (EI) m/e 327.1 ($M^+$); $^1$H-NMR ($CDCl_3$) δ ppm: 1.3–3.0 (br, 10H, BH), 2.15 (s, 3H, $CH_3$), 3.41 (s, 2H, $CH_2$), 7.06 (d, 2H, ArH, J=8.1 Hz), 7.48 (d, 2H, ArH, J=8.1 Hz).

Synthesis of Compound 2:

[4-(1-methyl-o-carboranyl)methyl]benzaldehyde (2): A solution of compound 1 (4.00 g, 12.23 mmol) in THF (150 mL) under Argon was cooled to −78° C. (acetone/dry ice bath). n-BuLi (7.6 mL, 1.6 M in hexane) was added dropwise while maintaining the temperature at −78° C. The reaction mixture was stirred for 30 minutes at −78° C. before dry DMF (5.0 mL, 64.6 mmol) was slowly added. The final mixture was stirred at −78° C. for 15 minutes and then warmed up slowly to room temperature. A 2N HCl solution (150 mL) was added end the reaction mixture stirred for 2 h at room temperature. The solution was then reduced to a volume of 200 mL and extracted with dichloromethane (4×50 mL). The organic extracts were washed once with an aqueous saturated solution of $NaHCO_3$, once with water and dried over anhydrous $Na_2SO_4$. After removal of the solvent under vacuum, the oily residue was purified by column chromatography on silica gel (dichloromethane/petroleum ether 1:1), yielding the title compound (2.1 g, 62% yield) as a white solid. MS (EI) m/e 276.2 ($M^+$); $^1$H-NMR ($CDCl_3$)

δ ppm: 1.5–3.0 (br, 10H, BH), 2.19 (s, 3H, CH$_3$), 3.54 (s, 2H, CH$_2$), 7.38 (d, 2H, ArH, J=8.0 Hz), 7.89 (d, 2H, ArH, J=8.0 Hz), 10.04 (s, 1H, CHO).

Synthesis of Compound 3:

meso-tetra[4(1-methyl-o-carboranyl)methylphenyl]porphyrin (3): A solution of aldehyde 2 (1.16 g, 4.19 mmol) and freshly distilled pyrrole (0.30 mL, 4.32 mmol) in dry dichloromethane (420 mL) was purged with Argon for 15 minutes. TFA (0.25 mL, 3.15 mmol) was added to the solution and the final mixture was stirred at room temperature under Argon for 20 hours (complete disappearance of starting compound 2 by TLC). After addition of p-chloranil (0.788 g, 3.14 mmol) the final reaction mixture was stirred at room temperature for 2 hours. The solution was concentrated under vacuum to 200 mL, then washed once with an aqueous saturated solution of NaHCO$_3$, and once with water before being dried over anhydrous Na$_2$SO$_4$. The residue obtained after removal of the solvent under vacuum was purified by column chromatography (dichloromethane/petroleum ether 1:1) and the fastest running porphyrin fraction was collected and recrystallized from dichloromethane/methanol, yielding 0.289 g (21% yield) of the title compound as purple crystals, m.p.>300° C.; MS (MALDI) m/e 1296.0 (M$^+$); $^1$H-NMR (CDCl$_3$) δ ppm: -2.80 (br, 2H, NH), 1.6–3.1 (br, 40H, BH), 2.34 (s, 12H, CH$_3$), 3.81 (s, 8H, CH$_2$), 7.59 (d, 8H, ArH, J=8.0 Hz), 8.20 (d, 8H, ArH, J=8.0 Hz), 8.85 (s, 8H, β-H). UV-Vis (CHCl$_3$) λ$_{max}$: 418 nm (ε 467,700), 514 (16,867), 550 (8,132), 590 (5,470), 646 (4,028).

Synthesis of Compound 4:

meso-tetra[4-(1-methyl-nido-carboranyl)methylphenyl]porphyrin tetrapotassium salt (4): Porphyrin 3 (0.050 g, 0.0386 mmol) was dissolved in a 3:1 mixture of pyridine and piperidine (4.0 mL), and stirred at room temperature in the dark for 36 hours, under Argon. The solvent was completely removed under vacuum, the residue re-dissolved in a 60% acetone aqueous solution and passed slowly through a Dowex 50W2-100 resin in the potassium form. The porphyrin fraction was collected, dried under vacuum, re-dissolved in a 30% acetone aqueous solution and again passed through the ion-exchange resin. After removal of the solvent under vacuum, the tetraanionic porphyrin was recrystallized from methanol/diethyl ether, yielding 0.051 g (94% yield) of the title compound, m.p.>300° C. $^1$H-NMR (CD$_3$COCD$_3$) δ ppm: -2.70 (s, 2H, NH), -2.45 to -1.90 (br, 4H, BH), 0.9–2.4 (br, 32H, BH), 1.59 (s, 12H, CH$_3$) 3.50 (s, 8H, CH$_2$), 7.81 (d, 8H, ArH, J=8.0 Hz), 8.08 (d, 8H, ArH, J=8.0 Hz), 8.90 (s, 8, β-H). UV-Vis (acetone) λ$_{max}$: 420 nm (ε 349,700), 516 (13,595), 554 (12,410), 594 (4,130), 650 (5,990).

Synthesis of Compound 5:

Zn(II)-meso-tetra[4-(1-methyl-o-carborane)methylphenyl]porphyrin (5): To a solution of porphyrin 3 (0.150 g, 0.110 mmol) in dichloromethane (150 mL), THF (10 mL), and pyridine (0.5 mL) was added ZnCl$_2$.2H$_2$O (0.075 mg, 0.435 mmol), and the final mixture was stirred at room temperature under Argon overnight. The mixture was then washed once with water, dried over anhydrous Na$_2$SO$_4$, and the solvent evaporated under vacuum. The residue was purified by column chromatography (dichloromethane/petroleum ether 1:1.5), the pink color fraction collected and recrystallized from dichloromethane/methanol, to give 0.135 g (92% yield) of the title compound as purple crystals, m.p.>300° C.; MS m/e 1358.6; $^1$H-NMR (CDCl$_3$) δ ppm: 1.6–3.0 (br, 40H, BH), 2.33 (s, 12H, CH$_3$), 3.80 (s, 8H, CH$_2$), 7.57 (br s, 8H, ArH), 8.19 (br s, 8H, ArH), 8.95 (br s, 8H, β-H). UV-Vis (CHCl$_3$) λ$_{max}$: 424 nm (ε 577,000), 554 (20,102), 596 (6,380).

Synthesis of Compound 6:

Zn(II)-meso-tetra[4-(1-methyl-nido-carboranyl)methylphenyl]porphyrin tetrapotassium salt (6): The Zn(II) complex 5 (0.075 g, 0.055 mmol) was dissolved in a 3:1 mixture of pyridine and piperidine (4.0 mL), and stirred at room temperature in the dark for 36 hours, under Argon. The solvent was completely removed under vacuum, the residue re-dissolved in a 60% acetone aqueous solution and passed slowly through a Dowex 50W2-100 resin in the potassium form. The porphyrin fraction was collected, dried under vacuum, re-dissolved in a 30% acetone aqueous solution and again passed through the ion-exchange resin. After removal of the solvent under vacuum, the tetraanionic porphyrin was recrystallized from methanol/diethyl ether, yielding 0.078 g (96.x % yield) of the title compound, m.p.>300° C. $^1$H-NMR (CD$_3$COCD$_3$) δ ppm: -2.48 to -1.95 (br, 4H, BH), 0.9–2.4 (br, 32H, BH), 1.59 (s, 12H, CH$_3$), 3.50 (s, 8H, CH$_2$), 7.77 (d, 8H, ArH, J=8.0 Hz), 8.11 (d, 8H, ArH, J=8.0 Hz), 8.92 (s, 8H, β-H). UV-Vis (acetone) λ$_{max}$: 422 nm (ε 479,000), 554 (13,870), 596 (6,595).

Synthesis of Compound 7:

[3-(1-methyl-o-carboranyl)methyl]bromobenzene (7): A two-necked round bottom flask containing 1-methyl-o-carborane (3.00 g, 18.99 mmol) in dry THF (150 mL) was cooled down to 0° C. under Argon. n-BuLi (12.0 mL, 1.6 M in hexane) was added dropwise and the resulting mixture was stirred at 0° C. and then cooled down to -10° C. A solution of anhydrous LiI (0.350 g, 2.61 mmol) in THF (2.5 mL) was added, followed by a solution of 3-(bromomethyl)bromobenzene (5.00 g, 20.00 mmol) in THF (10 mL). After stirring at -10° C. for 15 minutes, the final reaction mixture was warmed to room temperature and stirred for 12 hours under Argon. The reaction mixture was then washed with water (2×25 mL), extracted with diethyl ether (3×25 mL) and dried over Na$_2$SO$_4$. The solvent was then removed under vacuum and the crude solid obtained was purified by column chromatography (silica gel, dichloromethane/petroleum ether 1:9) to give the title compound (4.25 g, 65.0% yield). MS (EI) m/e 327.1 (M$^+$); $^1$H-NMR (CDCl$_3$) δ ppm: 1.3–3.1 (br, 10H, BH), 2.16 (s, 3H, CH$_3$), 3.42 (s, 2H, CH$_2$), 7.13 (d, 1H, ArH, J=7.8 Hz), 7.23 (t, 1H, ArH, J=7.8 Hz), 7.33 (s, 1H, ArH), 7.47 (d, 1H, ArH, J=7.8 Hz).

Synthesis of Compound 8:

[3-(1-methyl-o-carboranyl)methyl]benzaldehyde (8): A solution of compound 7 (1.00 g, 3.06 mmol) in THF (25 mL) under Argon was cooled to -78° C. (acetone/dry ice bath). n-BuLi (2.0 mL, 1.6 M in hexane) was added dropwise while maintaining the temperature at -78° C. The reaction mixture was stirred for 30 minutes at -78° C. before dry DMF (1.0 mL, 17.5 mmol) was slowly added. The final mixture was stirred at -78° C. for 15 minutes and then warmed up slowly to room temperature. A 2N HCl solution (25 mL) was added and the reaction mixture stirred for 2 h at room temperature. The solution was then reduced to a volume of 200 mL and extracted with dichloromethane (4×50 mL). The organic extracts were washed once with an aqueous saturated solution of NaHCO$_3$, once with water and dried over anhydrous Na$_2$SO$_4$. After removal of the solvent under vacuum, the oily residue was purified by column chromatography on silica gel (dichloromethane/petroleum ether 1:1), yielding the title compound (0.668 g, 79.1% yield) as a white solid. MS (EI) m/e 276.2 (M$^+$); $^1$H-NMR (CDCl$_3$) δ ppm: 1.4–3.1 (br, 10H, BH), 2.19 (s, 3H, CH$_3$), 3.55 (s, 2H, CH$_2$), 7.48 (d, 1H, ArH, J=7.8 Hz), 7.56 (t, 1H, ArH, J=7.8 Hz), 7.70 (s, 1H, ArH), 7.85 (d, 1H, ArH, J=7.8 Hz), 10.04 (s, 1H, CHO).

Synthesis of Compound 9:

meso-tetra[3-(1-methyl-o-carboranyl)methylphenyl]porphyrin (9): A solution of aldehyde 8 (0.660 g, 2.39 mmol) and freshly distilled pyrrole (0.18 mL, 2.59 mmol) in dry dichloromethane (240 mL) was purged with Argon for 45 minutes. TFA (0.15 mL, 1.89 mmol) was added to the solution and the final mixture was stirred at room temperature under Argon for 18 hours. After addition of p-chloranil (0.440 g, 1.77 mmol) the final reaction mixture was stirred at room temperature for 3 hours. The organic solution was washed once with an aqueous saturated solution of $NaHCO_3$, and once with water before being dried over anhydrous $Na_2SO_4$. The residue obtained after removal of the solvent under vacuum was purified by column chromatography (dichloromethane/petroleum ether 1:1) and the porphyrin fraction was collected and recrystallized from dichloromethane/methanol, yielding 0.252 g (33% yield) of the title compound as purple crystals, m.p.>300° C.; MS (MALDI) m/e 1296.0 ($M^+$); $^1$H-NMR ($CDCl_3$) δ ppm: −2.84 (br, 2H, NH), 1.5–3.0 (br, 40H, BH), 2.20 (s, 12H, $CH_3$), 3.74 (s, 8H, $CH_2$), 7.62 (d, 4H, ArH), 7.74 (d, 4H, ArH), 8.05 (d, 4H, ArH), 8.18 (d, 4H, ArH), 8.84 (s, 8H, β-H). UV-Vis ($CHCl_3$) $\lambda_{max}$: 419 nm, 516, 548, 590, 646.

Synthesis of Compound 10:

meso-tetra[3-(1-methyl-nido-carboranyl)methylphenyl] porphyrin tetrapotassium salt (10): Porphyrin 9 (0.049 g, 0.0378 mmol) was dissolved in a 3:1 mixture of pyridine and piperidine (4.0 mL), and stirred at room temperature in the dark for 36 hours, under Argon. The solvent was completely removed under vacuum, the residue re-dissolved in a 60% acetone aqueous solution and passed slowly through a Dowex 50W2-100 resin in the potassium form. The porphyrin fraction was collected, dried under vacuum, re-dissolved in a 30% acetone aqueous solution and again passed through the ion-exchange resin. After removal of the solvent under vacuum, the tetraanionic porphyrin was recrystallized from methanol/diethyl ether, yielding 0.050 g (94% yield) of the title compound, m.p.>300° C. UV-Vis (acetone) $\lambda_{max}$: 431 nm, 511, 546, 590, 647.

Synthesis of Compound 11:

4-Ethynylbenzaldehyde (11): To a solution of 4-bromobenzaldehyde (10.00 g, 54.08 mmol) and triphenylphosphine (0.500 g, 1.91 mmol) in anhydrous triethylamine (80 mL) under Angon, were added ethynyltrimethylsilane (6.00 g, 61.09 mmol) and palladium (II) acetate (0.100 g, 0.445 mmol). The final mixture was heated to reflux for 2 hours, and then it was cooled down to room temperature and filtrated. The filtrate was concentrated under vacuum to a thick oil, which was purified by column chromatography (dichloromethane/petroleum ether 1:4) and recrystallized from cold cyclohexane to give 10.5 g (96.1% yield) of 4-(trimethylsilylethynyl)benzaldehyde; MS m/e 187.2 ($M^+$); $^1$H-NMR ($CDCl_3$) δ ppm: 0.27 (s, 9H, $SiMe_3$), 7.60 (d, 2H, ArH, J=8.1 Hz), 7.82 (d, 2H, ArH, J=8.1 Hz), 10.00 (s, 1H, CHO)]. This compound (8.00 g, 39.59 mmol) was treated with $K_2CO_3$ (0.500 g) in methanol (50 mL) at 25° C. for 2 hours, under Argon. The solvent was removed under vacuum and the residue dissolved in dichloromethane (100 mL). This solution was washed once with an aqueous saturated solution of $NaHCO_3$ and once with water, before being dried over anhydrous $Na_2SO_4$ and the solvent evaporated under vacuum. The yellow residue was purified by column chromatography using dichloromethane/petroleum ether 1:4 for elution and recrystallization from cold cylohexane to give 4.40 g (85.5% yied) of the title compound; MS (EI) m/e 130.0; ($M^+$). $^1$H-NMR ($CDCl_3$) δ ppm: 3.30 (s, 1H, CH), 7.64 (d, 2H, ArH, J=8.1 Hz), 7.84 (d, 2H, ArH, J=8.1 Hz), 10.02 (s, 1H, CHO).

Synthesis of Compound 12:

4-(o-carboranyl)benzaldehyde (12): $BF_3.OEt_2$ (0.654 g, 4.62 mmol) was added at 0° C. and under Argon, to a solution of 4-ethynylbenzaldehyde (11) (6.00 g, 46.15 mmol) and 1,2-ethanedithiol (5.00 g, 53.09 mmol). This mixture was stirred at room temperature under Argon for 15 minutes. The reaction mixture was then washed once with a 10% aqueous NaOH solution, and once with an aqueous saturated solution of NaCl, before being dried over anhydrous $Na_2SO_4$ and the solvent evaporated under vacuum. Purification of the resulting residue by column chromatography (dichloromethane/petroleum ether 1:4) gave p-ethynylbenzyl(1,3-dithiane) (7.5 g, 79% yield) as a yellow solid [MS (EI) m/e 206.0 ($M^+$); $^1$H-NMR ($CDCl_3$) □ ppm: 3.07 (s, 1H, CH), 3.38 and 3.51 (m, 2H each, $CH_2CH_2$), 5.61 (s, 1H, SCH), 7.42 (d, 2H, ArH, J=8.1 Hz), 7.47 (d, 2H, ArH, J=8.1 Hz)]. Decaborane (3.00 g, 24.59 mmol), ethyl sulfide (5.00 g, 55.44 mmol) and dry toluene (50 mL) were combined in a schlenk tube equipped with a stir bar. This solution was heated at 40° C. for 3 hours and at 60° C. for 2 hours, and then allowed to cool down to room temperature. To this mixture was added a solution of p-ethynylbenzyl(1, 3-dithiane) (5.00 g, 24.26 mmol) in dry toluene (10 mL), and the final reaction mixture was slowly warmed up to 80° C. and stirred at this temperature for 3 days. After cooling to room temperature, the mixture was concentrated under vacuum and the resulting oil was dissolved in methanol (250 mL) and heated to reflux until liberation of hydrogen ceased (approximately 60 minutes). At room temperature a 50% aqueous HCl solution (2 to 3 mL) was cautiously added and the mixture was again heated to reflux until the hydrogen evolution was complete (approximately 30 minutes). After cooling down to room temperature, the reaction mixture was diluted with ethanol and excess ethylsulfide was removed by ethanol-ethylsulfide co-distillation. The remain residue was concentrated under vacuum. To a solution of the resulting residue in benzene (100 mL) at 5° C., was added 100 mL of a cold 10% aqueous NaOH solution, and the final mixture stirred vigorously for 15 minutes. The organic layer was separated, washed with water (3×25 mL) and dried over anhydrous $Na_2SO_4$. After evaporation of the solvent, the residue obtained was purified by column chromatography (dichloromethane/petroleum ether 1:4), yielding 5.25 g (66.8% yield) of p-(o-carboranyl)benzyl(1,3-dithiane) [MS (EI) m/e 324.1 ($M^+$); $^1$H-NMR ($CDCl_3$) δ ppm: 1.6–3.3 (br, 10H, BH), 3.36 and 3.47 (m, 2H each, $CH_2CH_2$), 3.91 (br s, 1H, o-carborane-CH), 5.56 (s, 1H, SCH), 7.40 (d, 2H, ArH, J=8.1 Hz), 7.46 (d, 2H, ArH, J=8.1 Hz)]. To a solution of the latter compound (5.00 g, 15.43 mmol) in 5% aqueous THF (25 mL) under Argon, was added dropwise a solution of $HgClO_4$ (12.50 g, 31.29 mmol) in THF (15 mL). The final mixture was stirred at room temperature for 15 minutes, before being filtered and the precipitate washed 3 times with 25 mL of diethyl ether. The filtrate was washed with an aqueous saturated solution of $Na_2CO_3$ (3×25 mL) and with water (2×25 mL), before being dried over anhydrous $Na_2SO_4$. The residue obtained after evaporation of the solvent was purified by column chromatography (dichloromethane/petroleum ether 1:4) to give the title compound (3.27 g, 85.6% yield); MS (EI) m/e 248.2 ($M^+$); $^1$H-NMR ($CDCl_3$) δ ppm: 1.60–3.2 (br, 10H, BH), 4.03 (br s, 1H, o-carborane-CH), 7.65 (d, 2H, ArH, J=8.4 Hz), 7.86 (d, 2H, ArH, J=8.4 Hz), 10.04 (s, 1H, CHO).

Synthesis of Compound 13:

meso-tetra[4-(o-carboranyl)phenyl]porphyrin (13): A solution of aldehyde 12 (1.05 g, 4.23 mmol) and freshly distilled pyrrole (0.30 mL, 4.32 mmol) in dry dichloromethane (430 mL) was purged with Argon for 30 minutes. TFA (0.20 mL, 2.52 mmol) was added to the solution and the final mixture was stirred at room temperature under Argon for 24 hours. After addition of p-chloranil (0.780 g, 3.14 mmol) the final reaction mixture was stirred at room temperature for 3 hours. The solution was concentrated under vacuum to 300 mL, then washed once with an aqueous saturated solution of $NaHCO_3$, and once with water before being dried over anhydrous $Na_2SO_4$. After evaporation of the solvent under vacuum, the resulting residue was purified by column chromatography (dichloromethane/petroleum ether 1:2) and the fastest running porphyrin fraction was collected and recrystallized from dichloromethane/methanol, yielding 0.220 g (17.7% yield) of the title compound as purple crystals, m.p.>300° C.; MS (MALDI) m/e 1184.5 (M+1); $^1$H-NMR ($CDCl_3$) δ ppm: −2.89 (br, 2H, NH), 1.7–3.5 (br, 40H, BH), 4.28 (br s, 4H, o-carborane-CH), 7.89 (d, 8H, ArH, J=8.0 Hz), 8.17 (d, 8H, ArH, J=8.0 Hz), 8.78 (s, 8H, β-H). $^1$H-NMR (d-TFA/$CDCl_3$) δ ppm: −0.97 (br, 4H, NH), 1.8–3.4 (br, 40H, BH), 4.31 (br s, 4H, o-carborane-CH), 8.13 (d, 8H, ArH, J=8.0 Hz), 8.51 (d, 8H, J=8.0 Hz), 8.68 (s, 8H, β-H). UV-Vis ($CHCl_3$) $\lambda_{max}$: 418 nm (ε 464,700), 514 (17,165), 550 (8,300), 590 (5,635), 646 (4,035).

Synthesis of Compound 14:

meso-tetra[4-(nido-carboranyl)phenyl]porphyrin tetrapotassium salt (14): Porphyrin 13 (0.0500 g, 0.0423 mmol) was dissolved in a 3:1 mixture of pyridine and piperidine (4.0 mL), and stirred at room temperature in the dark for 36 hours, under Argon. The solvent was completely removed under vacuum, the residue re-dissolved in a 60% acetone aqueous solution and passed slowly through a Dowex 50W2-100 resin in the potassium form. The porphyrin fraction was collected, dried under vacuum, re-dissolved in a 30% acetone aqueous solution and again passed through the ion-exchange resin. After removal of the solvent under vacuum, the tetraanionic porphyrin was recrystallized from methanol/diethyl ether, yielding 0.0494 g (90.2% yield) of the title compound, m.p.>300° C. $^1$H-NMR ($CD_3COCD_3$) δ ppm: −2.78 (s, 2H, NH), −2.45 to −1.90 (br, 4H, BH), 0.8–2.4 (br, 32H, BH), 2.57 (br s, 4H, nido-carborane-CH), 7.66 (d, 8H, ArH, J=8.0 Hz), 7.97 (d, 8H, ArH, J=8.0 Hz), 8.87 (s, 8H, β-H). UV-Vis (acetone) $\lambda_{max}$: 420 nm (ε 302,900), 516 (11,560), 554 (10,580), 594 (3,335), 650 (4,875).

Synthesis of Compound 15:

Zn(II)-meso-tetra[4-(o-carboranyl)phenyl]porphyrin (15): To a solution of porphyrin 13 (0.085 g, 0.072 mmol) in dichloromethane (50 mL), THF (4.0 mL), and pyridine (0.5 mL) was added $ZnCl_2.2H_2O$ (0.30 g), and the final mixture was stirred at room temperature under Argon overnight. The mixture was then washed once with water, dried over anhydrous $Na_2SO_4$, and the solvent evaporated under vacuum. The residue was purified by column chromatography (dichloromethane/cyclohexane 1:2), the pink color fraction collected and recrystallized from dichloromethane/methanol, to give 0.085 g (94.7% yield) of the title compound as purple crystals, m.p.>300° C.; MS (MALDI) m/e 1246.7 (M+); $^1$H-NMR ($CDCl_3$) δ ppm: 1.6–3.6 (br, 40H, BH), 4.30 (br s, 4H, o-carborane-CH), 7.91 (br s, 8H, ArH), 8.17 (br s, 8H, ArH), 8.88 (br s, 8H, β-H). UV-Vis ($CH_2Cl_2$) $\lambda_{max}$: 424 nm (ε 607,400), 554 (22,566), 594 (6,781).

Synthesis of Compound 16:

Zn(II)-meso-tetra[4-(nido-carboranyl)phenyl]porphyrin tetrapotassium salt (16): The Zn(II) complex 15 (0.0600 g, 0.0481 mmol) was dissolved in a 3:1 mixture of pyridine and piperidine (4.0 mL), and stirred at room temperature in the dark for 36 hours, under Argon. The solvent was completely removed under vacuum, the residue re-dissolved in a 60% acetone aqueous solution and passed slowly through a Dowex 50W2-100 resin in the potassium form. The porphyrin fraction was collected, dried under vacuum, re-dissolved in a 30% acetone aqueous solution and again passed through the ion-exchange resin. After removal of the solvent under vacuum, the tetraanionic porphyrin was recrystallized from methanol/diethyl ether, yielding 0.0615 g (94.0% yield) of the title compound; $^1$H-NMR ($CD_3COCD_3$) δ ppm: −2.54 to −1.78 (br, 4H, BH), 0.6–2.2 (br, 32H, BH), 2.58 (br s, 4H, nido-carborane-CH), 7.64 (d, 8H, ArH, J=8.1 Hz), 7.95 (d, 8H, ArH, J=8.1 Hz), 8.88 (s, 8H, β-H). UV-Vis (acetone) $\lambda_{max}$: 426 nm (ε 432,000), 558 (14,380), 598 (9,513).

Synthesis of Compound 17:

3-Ethynylbenzaldehyde (17): To a solution of 3-bromobenzaldehyde (10.00 g, 54.08 mmol) and triphenylphosphine (0.500 g, 1.91 mmol) in anhydrous triethylamine (100 mL) under Argon, were added ethynyltrimethylsilane (6.00 g, 61.09 mmol) and palladium (II) acetate (0.100 g, 0.445 mmol). The final mixture was heated to reflux for 2 hours, and then it was cooled down to room temperature and filtered. The filtrate was concentrated under vacuum to a thick oil, which was purified by column chromatography (dichloromethane/petroleum ether 1:4) to give 8.52 g (78.0% yield) of 3-(trimethylsilylethynyl)benzaldehyde [$^1$H-NMR ($CDCl_3$) δ ppm: 0.26 (s, 9H, $SiMe_3$), 7.47 (t, 1H, ArH, J=7.5 Hz), 7.70 (d, 1H, ArH, J=7.5 Hz), 7.82 (d, 1H, ArH, J=7.5 Hz), 7.96 (s, 1H ArH), 9.98 (s, 1H, CHO)]. This compound (5.00 g, 24.74 mmol) was treated with $K_2CO_3$ (0.500 g) in methanol (50 mL) at 25° C. for 2 hours, under Argon. The solvent was removed under vacuum and the residue dissolved in dichloromethane (100 mL). This solution was washed once with an aqueous saturated solution of $NaHCO_3$ and once with water, before being dried over anhydrous $Na_2SO_4$ and the solvent evaporated under vacuum. The yellow residue was purified by column chromatography using dichloromethane/petroleum ether 1:4 for elution and recrystallization from cyclohexane to give 2.80 g (87.1% yied) of the title compound; MS (EI) m/e 130.0; (M+). $^1$H-NMR ($CDCl_3$) δ ppm: 3.20 (s, 1H, CH), 7.51 (t, 1H, ArH, J=7.8 Hz), 7.74 (d, 1H, ArH, J=7.8 Hz), 7.87 (d, 1H, ArH, J=7.8 Hz), 7.99 (s, 1H, ArH), 10.02 (s, 1H, CHO).

Synthesis of Compound 18:

3-(o-carboranyl)benzaldehyde (18): $BF_3.OEt_2$ (0.11 g, 0.77 mmol) was added at 0° C. and under Argon, to a solution of 3-ethynylbenzaldehyde (17) (1.00 g, 7.69 mmol) and 1,2-ethanedithiol (0.73 g, 7.75 mmol). This mixture was stirred at room temperature under Argon for 15 minutes. The reaction mixture was then washed once with a 10% aqueous NaOH solution, once with an aqueous saturated solution of $NaHCO_3$ and once with water, before being dried over anhydrous $Na_2SO_4$ and the solvent evaporated under vacuum. Purification of the resulting residue by column chromatography (dichloromethane/petroleum ether 1:4) gave 1.28 g (80.7% yield) of m-ethynylbenzyl(1,3-dithiane) [MS (EI) m/e 206.0 (M+); $^1$H-NMR ($CDCl_3$) □ ppm: 3.07 (s, 1H, CH), 3.37 and 3.50 (m, 2H each, $CH_2CH_2$), 5.59 (s, 1H, SCH), 7.27 (t, 1H, ArH, J=7.8 Hz), 7.38 (d, 1H, ArH, J=7.8 Hz), 7.50 (d, 1H, ArH, J=7.8 Hz), 7.66 (s, 1H, ArH)]. Decaborane (0.0500 g, 4.10 mmol), ethyl sulfide (0.750 g, 8.32 mmol) and dry toluene (25 mL) were combined in a schlenk tube equipped with a stir bar. This solution was heated at 40° C. for 3 hours and at 60° C. for 2 hours, and then allowed to cool down to room temperature. To this mixture was added a solution of m-ethynylbenzyl(1,3-dithiane) (0.800 g, 3.88 mmol) in dry toluene (5 mL), and the final reaction mixture was slowly warmed up to 80° C. and stirred at this temperature for 3 days. After cooling to room temperature, the mixture was concentrated under vacuum and the resulting oil was dissolved in methanol (100 mL) and heated to reflux until liberation of hydrogen subsisted (approximately 60 minutes). At room temperature a 50% aqueous HCl solution (1.0 mL) was cautiously added and the mixture was again heated to reflux until the hydrogen evolution was complete (approximately 30 minutes). After cooling down to room temperature, the reaction mixture was diluted with ethanol and the excess ethylsulfide was removed by ethanol-ethylsulfide co-distillation. The remaining residue was concentrated under vacuum. To a solution of the resulting residue in benzene (50 mL) at 5° C., was added 100 mL of a cold 10% aqueous NaOH solution, and the final mixture stirred vigorously for 15 minutes. The organic layer was separated, washed with water (3×15 mL) and dried over anhydrous $Na_2SO_4$. After evaporation of the solvent, the residue obtained was purified by column chromatography (dichloromethane/petroleum ether 1:4), yielding 0.905 g (72.0% yield) of m-(o-carboranyl)benzyl(1,3-dithiane) [$^1$H-NMR ($CDCl_3$) δ ppm: 1.40–3.20 (br, 10H, BH), 3.39 and 3.49 (m, 2H each, $CH_2CH_2$), 3.97 (br s, 1H, o-carborane-CH), 5.58 (s, 1H, SCH), 7.28 (t, 1H, ArH, J=7.8 Hz), 7.39 (d, 1H , ArH, J=7.8 Hz), 7.55 (d, 1H, ArH, J=7.8 Hz), 7.63 (s, 1H, ArH)]. To a solution of the latter compound (1.00 g, 3.09 mmol) in 5% aqueous THF (10 mL) under Argon, was added dropwise a solution of $HgClO_4$ (2.50 g, 6.26 mmol) in THF (5.0 mL). The final mixture was stirred at room temperature for 15 minutes, before being filtered and the precipitate washed with 25 mL of diethyl ether. The filtrate was then washed with an aqueous saturated solution of $Na_2CO_3$ (3×10 mL) and with water (2×10 mL), before being dried over anhydrous $Na_2SO_4$. The residue obtained after evaporation of the solvent was purified by column chromatography (dichloromethane/petroleum ether 1:4) to give the title compound (0.677 g, 88.5% yield); $^1$H-NMR ($CDCl_3$) δ ppm: 1.5–3.3 (br, 10H, BH), 4.04 (br s, 1H, o-carborane-CH), 7.56 (t, 1H, ArH, J=7.8 Hz), 7.79 (d, 1H, ArH, J=7.8 Hz), 7.91 (d, 1H, ArH, J=7.8 Hz), 7.96 (s, 1H, ArH), 10.02 (s, 1H, CHO).

Synthesis of Compound 19:

meso-tetra[3-(o-carboranyl)phenyl]porphyrin (19): A solution of aldehyde 18 (0.702 g, 2.83 mmol) and freshly distilled pyrrole (0.200 mL, 2.88 mmol) in dry dichloromethane (285 mL) was purged with Argon for 30 minutes. TFA (0.100 mL, 1.26 mmol) was added to the solution and the final mixture was stirred at room temperature under Argon for 18 hours. After addition of p-chloranil (0.522 g, 2.10 mmol) the final reaction mixture was stirred at room temperature for 3 hours. The solution was concentrated under vacuum to 200 mL, then washed once with water, once with an aqueous saturated solution of $NaHCO_3$, and again once with water before being dried over anhydrous $Na_2SO_4$. After evaporation of the solvent under vacuum, the resulting residue was purified by column chromatography (dichloromethane/petroleum ether 1:2) and the fastest running porphyrin fraction was collected and recrystallized from dichloromethane/methanol, yielding 0.140 g (16.7% yield) of the title compound as purple crystals; MS (MALDI) m/e 1184. $^1$H-NMR ($CDCl_3$) δ ppm: −2.88 (br, 2H, NH), 1.6–3.5 (br, 40H, BH), 4.19 (br s, 4H, o-carborane-CH), 7.78 (m, 4H, ArH), 7.94 (m, 4H, ArH), 8.27 (m, 4H, ArH), 8.33 (m, 4H, ArH), 8.80 (s, 8H, β-H), UV-Vis ($CHCl_3$ Imax: 418 nm, 512, 549, 588, 644.

Synthesis of Compound 20:

meso-tetra[3-nido-carboranyl)phenyl]porphyrin tetrapotassium salt (20): Porphyrin 19 (0.010 g, 0.008 mmol) was dissolved in a 3:1 mixture of pyridine and piperidine (4.0 mL), and stirred at room temperature in the dark for 36 hours, under Argon. The solvent was completely removed under vacuum, the residue re-dissolved in a 60% acetone aqueous solution and passed slowly through a Dowex 50W2-100 resin in the potassium form. The porphyrin fraction was collected, dried under vacuum, re-dissolved in a 30% acetone aqueous solution and again passed through the ion-exchange resin. After removal of the solvent under vacuum, the tetraanionic porphyrin was recrystallized from methanol/diethyl ether, yielding 0.0108 g (98.1% yield) of the title compound, m.p.>300° C. 1H-NMR ($CD_3COCD_3$) d ppm: −2.70 (s, 2H, NH), −2.40 to −1.90 (br, 4H, BH), 0.8–2.3 (br, 32H, BH), 2.48 (br s, 4H, nido-carborane-CH), 7.49 (m, 4H, ArH), 7.65 (m, 4H, ArH), 7.84 (m, 4H, ArH), 8.15 (m, 4H, ArH), 8.88 (s, 8H, b-H). UV-Vis (acetone) Imax: 416 nm (e 326,300), 512 (14,300), 547 (8,000), 590 (4,300), 646 (4,300).

Synthesis of Compound 21:

Bis-(3,5-bromomethyl)bromobenzene (21): To a refluxing solution of 3,5-dimethylbromobenzene (4.63 g, 25.0 mmol) in dry $CCl_4$ (300 mL) under Argon, were added NBS (9.79 g, 55.0 mmol) and benzoyl peroxide (0.80 g, 3.30 mmol) in portions, over a one hour period. The final reaction mixture was refluxed with stirring and under Argon for 16 hours. After cooling to room temperature, the reaction mixture was filtered and the filtrate washed once with an aqueous saturated solution of $NaHCO_3$ and once with water. The organic solution was dried over anhydrous $Na_2SO_4$ and the solvent evaporated under vacuum. The resulting residue was purified by column chromatography using dichloromethane/petroleum ether 1:9 for elution, and the main product collected and recrystallized from n-hexane, yielding 2.83 g (33% yield) of the title and literature known compound; $^1$H-NMR ($CDCl_3$) δ ppm: 4.40 (s, 2H, CH2), 7.34 (s, 1H), 7.47 (s, 2H).

Synthesis of Compound 22:

Bis[3,5-(1-methyl-o-carboranyl)methyl]bromobenzene (22): n-BuLi (5.2 mL, 1.6 M in hexane) was added dropwise to a solution of methyl-o-carborane (1.39 g, 8.80 mmol) in dry THF (80 mL), at a temperature between −5° and 0° C., under Argon. The mixture was stirred at this temperature range for one and a half hours, then cooled to −15°-−20° C. (ice/salt bath). A solution of LiI (0.166 g, 1.27 mmol) in dry THF (15 mL) and a solution of compound 21 (1.37 g, 4.00 mmol) in dry THF (20 mL) were added and the final reaction mixture allowed to warm up to room temperature and stirred for 16 hours. After quenching the reaction with water the resulting mixture was extracted with diethyl ether. The organic extracts were washed once with water, once with brine, dried over anhydrous $Na_2SO_4$ and the solvent removed under vacuum. The crude product was purified by column chromatography using dichloromethane/petroleum ether 2:8 for elution, and the main product collected and recrystallized from n-hexane to give 1.26 g (63% yield) of the title compound; MS m/e 497.3; $^1$H-NMR ($CDCl_3$) δ ppm: 1.4–3.0 (br, 20H, BH), 2.17 (s, 6H, $CH_3$), 3.43 (s, 4H, $CH_2$), 6.96 (s, 1H), 7.31 (s, 2H).

Synthesis of Compound 23:

Bis[3,5-(1-methyl-o-carboranyl)methyl]benzaldehyde (23): A solution of compound 22 (0.994 g, 2.00 mmol) in THF (20 mL) under Argon was cooled to −78° C. n-BuLi (1.4 mL, 1.6 M in hexane) was added dropwise via syringe. After stirring the reaction mixture for 30 minutes at −78° C., dry DMF (0.77 mL, 10.x mmol) was slowly added. The resulting yellow mixture was stirred at −78° C. for 30 minutes and then warmed to 0° C. and stirred at this temperature for one hour. temperature. A 5% aqueous HCl solution was added until the pH of the reaction mixture was between 2 and 3, and the final mixture stirred at room temperature for 30 minutes. The aqueous layer was extracted 4 times with diethyl ether, the organic fraction dried over anhydrous $MgSO_4$ and the solvent evaporated under vacuum. Purification by column chromatography (dichloromethane/petroleum ether 2:3), afforded the title compound (0.632 g) in 70.9% yield; MS m/e 446.4; $^1$H-NMR ($CDCl_3$) δ ppm: 1.5–3.0 (br, 20H, BH), 2.20 (s, 6H, $CH_3$), 3.55 (s, 4H, $CH_2$), 7.30 (d, 1H, J=1.6 Hz), 7.67 (d, 2H, J=1.6 Hz), 10.03 (s, 1H, CHO).

Synthesis of Compound 24:

meso-tetra[bis-3,5-(1-methyl-o-carboranyl)methylphenyl]porphyrin (24): A solution of aldehyde 23 (0.243 g, 0.54 mmol) and freshly distilled pyrrole (0.050 mL g, 0.72 mmol) in dry dichloromethane (55 mL) was purged with Argon for 15 minutes. TFA (0.03 mL, 0.377 mmol) was added and the final solution was stirred at room temperature overnight (until complete disappearance of the starting aldehyde and formation of 2 new spots by TLC). After oxidation with p-chloranil (0.102 g, 0.41 mmol) for 6 hours at room temperature, the final reaction mixture was washed once with an aqueous saturated solution of $NaHCO_3$ and once with water, before being dried over anhydrous $Na_2SO_4$. The residue obtained after removal of the solvent was purified by column chromatography using dichloromethane/petroleum ether 1:2 for elution. The porphyrin fraction obtained was recrystallized from dichloromethane/methanol, to give 0.30 g (12% yield) of the title compound; MS m/e 1977.3 $^1$H-NMR (d-TFA/$CDCl_3$) δ ppm: −0.80 (br, NH), 1.5–3.1 (br, 80H, BH), 2.31 (s, 24H, $CH_3$), 3.91 (s, 16H, $CH_2$), 7.72 (s, 4H), 8.33 (s, 8H), 8.74 (s, 8H, β-H).

Synthesis of Compound 26:

5,15-bis[bis-3,5-(1-methyl-o-carboranyl)methylphenyl]porphyrin (26): A solution of aldehyde 23 (0.446 g, 1.00 mmol) and dipyrromethane 25 (0.146 g, 1.00 mmol) in dry dichloromethane (100 mL) was purged with Argon for 15 minutes and cooled down to 0° C. TFA (0.05 mL, 0.629 mmol) was added to the solution and the final mixture was stirred at 0° C. for 2 hours and then at room temperature overnight. After oxidation with p-chloranil (0.277 g, 1.13 mmol) for 6 hours at room temperature, the final reaction mixture was washed once with an aqueous saturated solution of $NaHCO_3$, once with water, and once with brine, before being dried over anhydrous $MgSO_4$. The residue obtained after removal of the solvent was purified by column chromatography (alumina) using dichloromethane for elution. The porphyrin fraction obtained was recrystallized from acetone to give 33.6% yield (0.192 g) of the title compound; MS m/e 1144.0; $^1$H-NMR (d-TFA/$CDCl_3$) δ ppm: −1.92 (br, NH), 1.4–3.2 (br, 40H, BH), 2.30 (s, 12H, $CH_3$), 3.89 (s, 8H, $CH_2$), 7.71 (s, 2H), 8.34 (s, 4H) β-H, J=4.5 Hz), 9.61 (d, 4H, β-H, J=4.5 Hz), 10.98 (s, 2H, meso-H).

Synthesis of Compound 27:

5,15-bis[bis-3,5-(1-methyl-nido-carboranyl)methylphenyl]porphyrin tetrapotassium salt (27): Porphyrin 26 (0.100 g, 0.087 mmol) was dissolved in a 3:1 mixture of pyridine and piperidine (4.0 mL), and stirred at room temperature in the dark for 36 hours, under Argon. The solvent was completely removed under vacuum, the residue re-dissolved in a 60% acetone aqueous solution and passed slowly through a Dowex 50W2-100 resin in the potassium form. The porphyrin, fraction was collected, dried under vacuum, re-dissolved in a 30% acetone aqueous solution and again passed through the ion-exchange resin. After removal of the solvent under vacuum, the tetraanionic porphyrin was recrystallized from methanol/diethyl ether, yielding 0.102 g (92.8% yield) of the title compound. $^1$H-NMR ($CD_3COCD_3$) δ ppm: −2.84 (s, 2H, NH), −2.45 to −1.85 (br, 4H, BH), 0.9–2.4 (br, 32H, BH), 1.66 (s, 12H, $CH_3$), 3.52 (s, 8H, $CH_2$), 7.67 (s, 1H, ArH), 7.74 (s, 1H, ArH), 8.37 (s, 4H, ArH), 9.53 (dd, 4H, β-H), 9.61 (dd, 4H, β-H), 10.58 (s, 2H, meso-H). UV-Vis (acetone) $λ_{max}$: 406 nm (ε 312,600), 502 (13,400), 536 (7,800), 576 (6,100), 630 (3,100).

Synthesis of Compound 28:

Zn(II)-5,15-bis[bis-3,5-(1-methyl-o-carboranyl)methylphenyl]porphyrin (28): To a solution of porphyrin 26 (0.065 g, 0.057 mmol) in dichloromethane (100 mL) and THF (10 mL), was added $ZnCl_2.2H_2O$ (0.031 g, 0.288 mmol), and the final mixture was stirred at room temperature under Argon overnight. The mixture was then washed once with water, dried over anhydrous $Na_2SO_4$, and the solvent evaporated under vacuum. The residue was purified by column chromatography (dichloromethane/cyclohexane 2:1), the pink color fraction collected and recrystallized from dichloromethane/methanol, to give 0.061 g (89.x % yield) of the title compound; MS (MALDI) m/e 1206.6. $^1$H-NMR ($CDCl_3$) δ ppm: 1.4–3.0 (br, 40H, BH), 2.11 (s, 12H, $CH_3$), 3.64 (s, 8H, $CH_2$) 7.33 (s, 2H, ArH), 7.98 (s, 4H, ArH), 8.98 (d, 4H, β-H, J=4.5 Hz), 9.41 (d, 4H, β-H, J=4.5 Hz), 10.25 (s, 2H, meso-H).

Synthesis of Compound 29:

Zn(II)-5,15-bis[bis-3,5-(1-methyl-nido-carboranyl)methylphenyl]porphyrin tetrapotassium salt (29): The Zn(II) complex 28 (0.050 g, 0.041 mmol) was dissolved in a 3:1 mixture of pyridine and piperidine (4.0 mL), and stirred at room temperature in the dark for 36 hours, under Argon. The solvent was completely removed under vacuum, the residue redissolved in a 60% acetone aqueous solution and passed slowly through a Dowex 50W2-100 resin in the potassium form. The porphyrin fraction was collected, dried under vacuum, re-dissolved in a 30% acetone aqueous solution and again passed through the ion-exchange resin. After removal of the solvent under vacuum, the tetraanionic porphyrin was recrystallized from methanol/diethyl ether, yielding 0.052 g (94.8% yield) of the title compound; $^1$H-NMR ($CD_3COCD_3$) δ ppm: −2.45 to −1.85 (br, 4H, BH), 0.9–2.4 (br, 32H, BH), 1.65 (s, 12H, $CH_3$), 3.50 (s, 8H, $CH_2$), 7.66 (s, 1H, ArH), 7.73 (s, 1H, ArH), 8.28 (s, 4H, ArH), 9.41 (dd, 4H, β-H), 9.47 (dd, 4H, β-H), 10.33 (s, 2H, meso-H). UV-Vis (acetone) $λ_{max}$: 412 nm (ε 263,100), 496 (1,400), 542 (9,900), 580 (1,070), MS (MALDI) m/e 1319.4.

Synthesis of Compound 30:

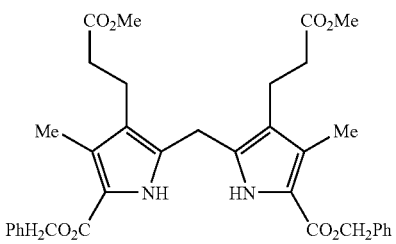

31

The Zn(II) complex of carboranyl compound 30 of FIG. 7, bearing four hydrophobic o-carboranes and four hydrophilic 3-hydroxypropyl side chains, was prepared from dipyrromethane 31 and benzaldehyde 23, in 28% overall yield. The benzyl ester groups of 31 were removed by catalytic hydrogenation ($H_2$—Pd/C), followed by decarboxylation using trifluoroacetic acid (TFA). Condensation of the resulting 1,9-diunsubstituted dipyrromethane with benzaldehyde 23, using Lindsey-type conditions (TFA as the acid catalyst and p-chloranil as the oxidizing agent), produced a tetra-propionic ester porphyrin in 40% yield. Metalation of this compound using zinc (II) chloride in dichloromethane, at room temperature, quantitatively produced the corresponding Zn(II) porphyrin. Reduction of the methyl ester groups with 5.2 equivalents of lithium aluminum hydride in tetrahydrofuran at 0° C., gave the Zn(II) complex of porphyrin 30 in 70% yield. The Zn(II) complex of 30 is soluble in methanol but only partially soluble in water.

In Vitro and In Vivo Analysis of Boronated Porphyrins

In vitro studies using rat 9L gliosarcoma cells, mouse B16 melanoma cells and human U-373MG glioblastoma cells have been performed. We found that all compounds studied have very low dark cytoxicities, are readily taken up and retained by cells and localize in specific cell organelles, mostly in close proximity to the cell nucleus.

Our biological results to date indicate that these compounds have very low in vivo toxicities. So far we have determined maximum tolerated doses (MTD) for 8 of our compounds using healthy female Balb/c mice, and for all compounds tested we found MTD >300 mg per Kg of body weight.

We have also done a biodistribution study with 2 of our compounds, using male Fisher 344 rats bearing 9L glioma tumors, and achieved tumor to normal brain boron concentration ratios of 5 and higher. This compares favorably with drugs currently in BNCT clinical trials—BSH and BPA—which both show lower selectivities, i.e. smaller ratios.

Cytotoxicity/Phototoxicity Assays

Human glioblastoma U373 MG and mouse melanoma B16 cells were obtained from ATCC. The rat gliosarcoma line was kindly provided by the UCSF Brain Tumor Research Group. All cells were maintained in log phase monolayer cultures with RPMI 1640 supplemented with 10% fetal bovine and 2 mM glutamine.

Cells were seeded in 96-well culture plates, allowed to settle and attach for 24–48 hours, and then triplicate wells were exposed to two fold serial dilutions of test compounds at concentrations up to 250 µM. Compounds 4, 6, 10, and the Zn(II) complex of 10 in crystalline form were carefully weighed and dissolved in 100% DMSO to prepare stock solutions; subsequent dilutions were done directly into the culture medium just prior to administration to cells. After short term (2 hours) or long term (24–48 hours) exposure, cells were washed and wells refilled with fresh culture medium. For dark toxicity trials cells were allowed to proliferate for an additional 48–72 hours. For phototoxicity trials, washed cells were irradiated for 10 minutes with broad spectrum (600–700 nm) red light and then returned to an incubator for 48–72 hours.

Exposure to drug for 2 hours followed by drug wash-out did not inhibit proliferation of any of the three cells types. Exposure for 24 hours was inhibitory only at higher concentrations ($IC_{50}$-$\geq$150 µM) for 9L and U-373 MG cells, but B16 viability was unaffected. Whereas the metal free porphyrins 4 and 10 display nearly identical $IC_{50}$ values (~150 µM) in the affected cells, their Zn(II) complexes were found to be about 20% less toxic ($IC_{50}$~180–185 µM), Thus, the nido-carboranylporphyrin compounds of the present invention display low dark toxicity.

For carboranylprorphyrin 4, irradiation with broad spectrum light caused cytotoxicity at 2 hours ($IC_{50}$=50 µM) and 24 hours exposure ($IC_{50}$=1.5 µM). As observed for the dark toxicity experiments, the corresponding Zn(II) complex 6 was about 20-fold less phototoxic. These phototoxicity results indicate that the carboranylporyphin compounds of the present invention would be active in PDT. As with dark toxicity, B16 cells were more resistant that the other two cell types.

Cellular Uptake and Retention

The concentration-dependent uptake of compounds 4, 6, 10 and the corresponding Zn(II) complex of 10 was investigated in cells exposed to 1, 5, and 10 µM of the porphyrins for 24 hours. The concentration of intracellular-bound porphyrin was determined by chemical extraction of washed cell monolayers, followed by spectrophotometric and/or IMP-MS determinations. The uptake values for 9L and U-373MG cells were very similar and exceeded that of B16 cells. The porphyrin accumulation invariably increased with increasing exogenous drug concentration and the uptake of nido-carboranylprophyrins 4 and 10 was approximately 4-times greater than that of the corresponding Zn(II) complexes.

The uptake of carboranylporphyrins by log phase cells was also shown to be time-dependent. Cells exposed to 5 µM drug concentrations contained increasing amounts of extractable porphyrin over the 24-hour uptake period examined in these studies. While 9L and U-373MG cells had similar uptake levels, B16 cell cultures consistently accumulated 60–70% less drug on a per cell basis. Cell-bound porphyrin that could not be removed by rinsing the cells with Hanks balanced salt solution (HBSS) was detectable as early as 1 hour after introducing drug to the cell culture. In experiments using 9L cell s exposed to a 10 µM concentration of free-base porphyrins 4 and 10, intracellular levels >60 µg of boron per billion cells (or gram of wet tissue) were achieved, following a 24 hour exposure to drug.

Intacellular Localization

Confocal fluorescence microscopy was used to examine the intracellular localization of nido-carboranylporphyrin 4 in live cells. Rat 9L tumor cells and human normal keratinocyte line HaCaT were used in these studies. HaCaT cells were included in these particular experiments because they adhere and spread nicely on glass cover slips, thus facilitating the imaging process. Cells exposed to 2 µM concentration of porphyrin 4 for either 6 or 24 hours were examined at a magnification of 200× for intracellular fluorescence using excitation/emission wavelengths optimized for this type of compound. The 9L and HaCaT cells showed a similar intracellular fluorescent pattern. In both cases, 100% of the cells were labeled and the cells exposed to drug for 24 hours were slightly brighter than those exposed for 6 hours. The punctuate fluorescence was predominantly perinuclear, with many cells having an additional local area of concentration that appeared to be adjacent to the nuclear membrane. No fluorescent signal was detectable in the plasma membranes of isolated individual cells nor in the intercellular junctions of confluent cells.

In Vivo Biodistribution

Male Fisher 344 rats with bilateral subcutaneous 9L tumors were injected i.v. (2.2 ml) with a 2 mM solution of carboranylporphyrin in 4% Cremophor/saline. Groups of three rats each were sacrificed at 2, 8, 18, 24 and 48 hours following drug administration. None of the rats showed any signs of discomfort or toxicity from injection of the nido-carboranylporphyrins. Plasma, tumor, and normal brain tissue boron levels were determined by IMP-MS. Rapid elimination of boron from plasma was observed between 2 and 8 hours. Boron concentrations in normal brain were always lower than those in tumor and a tumor to brain concentration ratio of 6 was seen at 8 hours following drug administration.

BIBLIOGRAPHY

The following references are each incorporated herein by reference:

Badary, O. A.; Al-Shabanah, O. A.; Al-Gharably, N. M.; Elmazar, M. M. *Anti-Cancer Drugs* 1998, 9, 809–515.

Barth, R. F.; Soloway, A. H.; Fairchild, R. G.; Brugger, R. M. *Cancer* 1992, 70, 2995 3007.

Barth, R. F.; Soloway, A. H.; Goodman, J. H.; Gahbauer, R. A.; Gupta, N.; Blue, T. E.; Yang, W.; Tjarks, W. *Neurosurg.* 1999, 44, 433–451.

Bonnett, R. *Chem. Soc. Rev.* 1995, 24, 19–33.

Capala, J.; Makar, M. S.; Coderre, J. A. *Radiation Res.* 1996, 146, 554–560.

Ceberg, C. P.; Brun, A.; Kahl, S. B.; Koo, M. S.; Persson, B. R. R.; Salford, L. G. *J. Neurosurg.* 1995, 83, 86–92.

Ding, L.; Etemad-Moghadam, G.; Cros, S.; Auclair, C.; Meunier, B. *J. Med. Chem.* 1991, 34, 900–906.

Dougherty, T. J.; Gomer, C. J.; Henderson, B. W.; Jori, G.; Kessel, D.; Korbelik, M.; Moan, J.; Peng, Q. *J. Natl. Cancer Inst.* 1998, 90, 889–905.

Elowitz, E. H.; Bergland, R. M.; Coderre, J. A.; Joel, D. D.; Chadha, M.; Chanana, A. D. *Neurosurgery* 1998, 42, 463–469.

Hawthorne, M. F. *Mol. Med. Today* 1998, 4, 174–181.

Hawthorne, M. F. *Angew. Chem. Int. Ed. Engl.* 1993, 32, 950–984.

Hill, J. S.; Kahl, S. B.; Kaye, A. H.; Stylli, S. S.; Koo, M.-S.; Gonzales, M. F.; Verdaxis, N. J.; Johnson, C. I. *Proc. Natl. Acad. Sci. USA* 1992, 89, 1785–1789.

Hill, J. S.; Kahl, S. B.; Stylli, S. S.; Nakamura, Y.; Koo, M.-S.; Kaye, A. H. *Proc. Natl. Acad. Sci. USA* 1995, 92, 12126–12130.

Kageji, T.; Nakagawa, Y.; Kitamura, K.; Matsumoto, K.; Hatanaka, H. *J. Neurooncol.* 1997, 33, 117–130.

Kahl, S. B.; Koo, M.-S. *J. Chem. Soc., Chem. Commun.* 1990, 1769–1771.

Luo Y.; Chang, C. K.; Kessel, D. *Photochem. Photobiol.* 1996, 63, 4, 528–534.

Luo Y.; Kessel, D. *Photochem. Photobiol.* 1997, 66, 4, 479–483.

Mang, T. S.; McGinnis, C.; Liebow, C.; Nseyo, U. O.; Crean, D. H.; Dougherty, T. J. *Cancer* 1993, 71, 269–276.

Matsumura, A.; Shibata, Y.; Yamamoto, T.; Yoshida, F.; Isobe, T.; Nakai, K.; Hayakawa, Y.; Kiriya, M.; Shimojo, N.;

Ono, K.; Sakata, I.; Nakajima, S.; Okumura, M.; Nose, T. *Cancer Lett.* 1999, 141, 203–209.

Miura, M.; Gabel, D.; Oenbrink, G.; Fairchild, R. G. *Tetrahedron Lett.* 1990, 31, 2247–2250.

Miura, M.; Micca, P. L.; Fisher, C. D.; Gordon, C. R.; Heinrichs, J. C.; Slatkin, D. N. *Br. J. Radiol.* 1998, 71, 773–781.

Munson, B. R.; Fiel, R. J. *Nucleic Acids Res.* 1992, 20, 1315–1319.

Nigg, D. W.; Wheeler, F. J.; Wessol, D. E.; Capala, J.; Chadha, M. *J. Neurooncol.* 1997, 33, 93–104.

Ozawa, T.; Afzal, J.; Wyrick, B. J.; Hu, L. J.; Lamborn, K. R.; Bollen, A. W.; Bauer, W. F.; Fike, J. R.; Phillips, T. L.; Blakely, E. A.; Kahl, S. B.; Deen, D. F. *Proc. Am. Assoc. Cancer Res.* 1998, 39, 586.

Penning, L. C.; Lagerberg, J. W.; Van Dierendonck, J. H.; Cornelisse, C. J.; Dubbelman, T. M.; Van Steveninck, J. *Cancer Res.* 1996, 54, 5561–5567.

Pignol, J.-P.; Oudart, H.; Chauvel, P.; Sauerwein, W.; Gabel, D.; Prevot, G. *Br. J. Radiol.* 1998, 71, 320–323.

Sari, M. A.; Battioni, J. P.; Dupré, D.; Mansuy, D.; Le Pecq, J. B. *Biochemistry* 1990, 29, 4205–4215.

Schneider, H.-J.; Wang, M. *J. Org. Chem.* 1994, 59, 7473–7478.

Schnitmaker, J. J.; Bass, P.; van Leengoed, M. L. L. M.; van der Meulen, F. W.; Star, W. M.; van Zaudwijk, N. *J. Photochem. Photobiol. B: Biol.* 1996, 34, 3–12.

Tolpin, E. I.; Wellum, G. R.; Berley, S. A. *Inorg. Chem.* 1978, 17, 2867–2873.

Woodburn, K. W.; Vardaxis, N. J.; Hill J. S.; Kaye, A. H. Phillips, D. R. *Photochem. Photobiol.* 1991, 54, 725–732.

Woodburn, K.; Phadke, A. S.; Morgan, A. R. *Bioorg. Med. Chem. Lett.* 1993, 3, 2017–1022.

Woodcock, D. M.; Jefferson, S.; Linsenmeyer, M. E.; Crowther, P. J.; Chojnowski, G. M.; Williams, B.; Bertoncello, I. *Cancer Res.* 1990, 50, 4199–4203.

What is claimed is:

1. A phenyl porphyrin compound wherein a carboranyl group is attached to a phenyl group by a carbon-carbon linkage.

2. The porphyrin compound of claim 1 corresponding to formula I:

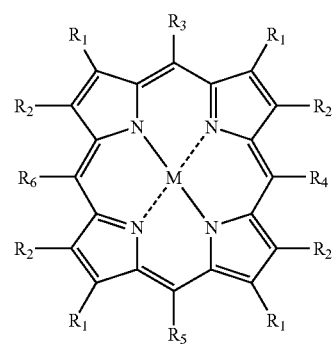

wherein M is 2H or a divalent metal ion; R1 and R2 are each independently hydrogen, alkyl or hydoxyalkyl; and R3 through R6 are hydrogen or a phenyl group of formula II:

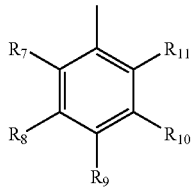

wherein R7 through R11 are hydrogen, a carboranyl group, said carboranyl group being attached to the phenyl group by a carbon-carbon linkage, or are selected from the group consisting of hydroxyl, $NMe_3^+$, $PMePh_2^+$, $PO(OH)_2$, $SO_3H$, COOH, and $NH_2$; and either one or two of R7 through R11 are other than hydrogen; and at least one of R3 through R6 is a phenyl group of formula II having at least one of said carboranyl groups.

3. The compound of claim 2 wherein said carboranyl group is 1-methyl-o-carboranyl or o-carboranyl.

4. The compound of claim 1 wherein the compound is at least about 15% boron by weight.

5. The compound of claim 4 wherein the compound is about 25% to about 44% boron by weight.

6. The compound of claim 2 wherein two of R3 through R6 are phenyl groups of formula II, each having at least one of said carboranyl groups.

7. The compound of claim 2 wherein R3 through R6 are phenyl groups of formula II, each having at least one of said carboranyl groups.

8. An intermediate for use in the synthesis of porphyrin compounds comprising a benzaldehyde of formula III

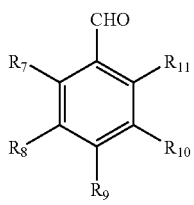

wherein R7 through R11 are each hydrogen, a carboranyl group, said carboranyl group being attached to the benzaldehyde by a carbon-carbon linkage, or are selected from the group consisting of hydroxyl, $NMe_3^+$, $PMePh_2^+$, $P(CH_2OH)_2$, $SO_3^-$, COOH, and $CO_2^-$; and two of R7 through R11 are said carboranyl groups.

9. The intermediate of claim 8 wherein the carboranyl group is 1-methyl-o-carboranyl or o-carboranyl.

10. A composition for use in boron neutron capture therapy or photodynamic therapy, comprising an effective amount of the porphyrin compound of claim 1, and a pharmaceutically acceptable carrier or excipient, wherein the effective amount is an amount sufficient for selective uptake, retention and damage to tumor cells when said tumor cells are irradiated by thermal neutrons or by red light.

11. A method of delivering an effective amount of a neutron capture agent to tumor cells, comprising contacting the tumor cells with the porphyrin compound of claim 1, wherein the tumor cells are glioblastoma, gliosarcoma, or melanoma tumor cells.

12. The method of claim 11 wherein the porphyrin compound is administered to a patient and selectively taken up by the tumor cells.

13. The method of claim 12 wherein the amount of porphyrin compound taken up by the tumor cells is an effective amount of the compound, wherein an effective amount is an amount sufficient for cytotoxicity when said tumor cells are irradiated by thermal neutrons.

14. A method of delivering an effective amount of a photosensitizing agent to tumor cells comprising contacting the tumor cells with the porphyrin compound of claim 1, wherein the tumor cells are glioblastoma, gliosarcoma, or melanoma tumor cells.

15. The method of claim 14 wherein the porphyrin compound is administered to a patient and selectively taken up by the tumor cells.

16. The method of claim 15 wherein the amount of porphyrin compound taken up by the tumor cells is an effective amount of the compound, wherein an effective amount is an amount sufficient for cytotoxicity when the tumor cells are irradiated by red light.

17. A method of making a porphyrin compound comprising the steps of:

a) providing a reaction mixture comprising a pyrrole or a dipyrrole, and a benzaldehyde dissolved in a suitable solvent, wherein the pyrrole or dipyrrole is unsubstituted or substituted with alkyl groups and the benzaldehyde is of formula III

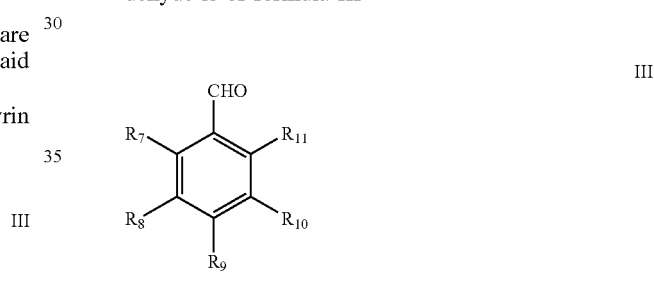

wherein R7 through R11 are each hydrogen, a carboranyl group, said carboranyl group being attached to the benzaldehyde by a carbon-carbon linkage, or are selected from the group consisting of hydroxyl, $NMe_3^+$, $PMePh_2^+$, $PO(OH)_2$, $P(CH_2OH)_2$, $SO_3^-$, COOH, $CO_2^-$, and $NH_2$; and b) subjecting the reaction mixture to an acidic pH until the benzaldehyde and the pyrrole or the benzaldehyde and the dipyrrole are converted to a porphyrin compound.

18. The method of claim 17 wherein the reaction mixture is subjected to an acidic pH by the addition of TFA.

19. The method of claim 17 further comprising oxidation of the reaction mixture with tetrachloroquinone or dichlorodicyanobenzoquinone.

20. The method of claim 17 further comprising complexing the porphyrin compound with a divalent metal ion.

21. The method of claim 17 further comprising forming a salt of the porphyrin compound.

22. The method of claim 17 wherein the solvent is dichloromethane.

23. The method of claim 17 wherein the carboranyl group is 1-methyl-o-carboranyl or o-carboranyl.

* * * * *